(12) United States Patent
Chen et al.

(10) Patent No.: US 9,510,940 B2
(45) Date of Patent: Dec. 6, 2016

(54) BIOABSORBABLE MULTILAYER NASAL VALVE SPREADER GRAFT

(75) Inventors: G. Gavin Chen, Hillsborough, NJ (US); Krasimira Hristov, Belle Mead, NJ (US); Jianxin Guo, Livingston, NJ (US); James A. Matrunich, Mountainside, NJ (US); Jianguo Jack Zhou, Bethlehem, PA (US)

(73) Assignee: Ethicon, Inc., Somerville, NJ (US)

(*) Notice: Subject to any disclaimer, the term of this patent is extended or adjusted under 35 U.S.C. 154(b) by 421 days.

(21) Appl. No.: 13/029,541

(22) Filed: Feb. 17, 2011

(65) Prior Publication Data
US 2012/0215307 A1    Aug. 23, 2012

(51) Int. Cl.
| *A61F 2/18* | (2006.01) |
| *A61M 29/00* | (2006.01) |
| *B29C 45/73* | (2006.01) |
| *A61B 17/80* | (2006.01) |

(52) U.S. Cl.
CPC ............ *A61F 2/186* (2013.01); *A61B 17/8061* (2013.01); *A61F 2210/0004* (2013.01); *A61F 2240/001* (2013.01); *B29C 45/73* (2013.01)

(58) Field of Classification Search
CPC .................................. A61F 2/18; A61M 29/00
USPC ........ 623/10–23.58; 606/146–148, 151, 157, 606/219, 199
See application file for complete search history.

(56) References Cited

U.S. PATENT DOCUMENTS

| 1,105,105 A | 7/1914 | Sherman |
| 3,978,185 A | 8/1976 | Buntin et al. |
| D261,935 S | 11/1981 | Halloran |
| 4,378,802 A | 4/1983 | Ersek |
| 4,429,690 A | 2/1984 | Angelino-Pievani |
| 4,457,756 A | 7/1984 | Kern et al. |
| 4,863,974 A | 9/1989 | Mallouk |
| 4,905,680 A | 3/1990 | Tunc |
| 4,938,234 A | 7/1990 | Capriotti |
| 4,994,084 A | 2/1991 | Brennan |
| 5,002,583 A | 3/1991 | Pitaru |
| 5,069,660 A | 12/1991 | Grantham |
| 5,112,353 A | 5/1992 | Johansson |
| 5,275,601 A | 1/1994 | Gogolewski |
| 5,413,600 A | 5/1995 | Mittelman |
| D366,526 S | 1/1996 | Rizzo |
| 5,496,371 A | 3/1996 | Eppley |
| 5,620,452 A | 4/1997 | Yoon |

(Continued)

FOREIGN PATENT DOCUMENTS

| CN | 2439847 | 7/2001 |
| CN | 1333006 | 1/2002 |

(Continued)

OTHER PUBLICATIONS

Samuel Stal, M.D. et al, "The Use of Resorbable Spacers for Nasal Spreader Grafts", Plastic and Reconstructive Surgery, Sep. 2000, vol. 106, No. 4, pp. 922-928.

(Continued)

*Primary Examiner* — Yashita Sharma

(57) ABSTRACT

Novel bioabsorbable, nasal spreader graft implant devices are disclosed. The devices are useful in rhinoplasty and nasal reconstruction surgical procedures, as well as other surgical procedures. The devices have biodegradable core plates and biodegradable spreader plates or tissue ingrowth plates. The plates may have tissue ingrowth properties.

34 Claims, 20 Drawing Sheets

(56) References Cited

U.S. PATENT DOCUMENTS

| | | | |
|---|---|---|---|
| 5,674,286 A | 10/1997 | D'Alessio | |
| 5,863,297 A | 1/1999 | Walter | |
| 5,868,746 A | 2/1999 | Sarver | |
| 6,106,541 A | 8/2000 | Hurbis | |
| 6,228,111 B1* | 5/2001 | Tormala et al. | 623/1.38 |
| 6,322,590 B1 | 11/2001 | Sillers | |
| 6,454,803 B1 | 9/2002 | Romo, III | |
| 6,516,806 B2 | 2/2003 | Knudson | |
| 7,740,630 B2* | 6/2010 | Michelson | 606/71 |
| 2002/0173848 A1 | 11/2002 | Sachs | |
| 2005/0015088 A1 | 1/2005 | Ringeisen | |
| 2005/0085817 A1 | 4/2005 | Ringeisen | |
| 2005/0288790 A1 | 12/2005 | Swords | |
| 2006/0224242 A1 | 10/2006 | Swords | |
| 2007/0061015 A1 | 3/2007 | Jensen | |
| 2007/0213828 A1 | 9/2007 | Trieu | |
| 2007/0270899 A1 | 11/2007 | aWengen | |
| 2007/0293946 A1 | 12/2007 | Gonzles et al. | |
| 2008/0058858 A1 | 3/2008 | Smith | |
| 2008/0077240 A1 | 3/2008 | Saidi | |
| 2008/0196729 A1* | 8/2008 | Browning | 128/834 |
| 2008/0234818 A1 | 9/2008 | Kang | |
| 2009/0062846 A1 | 3/2009 | Ken | |
| 2009/0069904 A1* | 3/2009 | Picha | 623/23.72 |
| 2009/0157194 A1 | 6/2009 | Shikinami | |
| 2009/0170927 A1* | 7/2009 | Bezwada | 514/455 |
| 2009/0177272 A1* | 7/2009 | Abbate et al. | 623/1.42 |
| 2009/0270308 A1 | 10/2009 | Libin et al. | |
| 2009/0292358 A1 | 11/2009 | Saidi | |
| 2010/0076555 A1 | 3/2010 | Marten | |
| 2010/0185282 A1 | 7/2010 | Jung | |
| 2012/0078367 A1 | 3/2012 | Hristov et al. | |
| 2012/0215307 A1 | 8/2012 | Chen et al. | |

FOREIGN PATENT DOCUMENTS

| | | |
|---|---|---|
| CN | 201418793 | 3/2010 |
| DE | 20307058 U1 | 9/2003 |
| DE | 202004021075 U1 | 9/2006 |
| DE | 102006023058 | 10/2007 |
| EP | 1475056 A1 | 11/2004 |
| EP | 1475056 B1 | 10/2010 |
| JP | 2010-104791 | 5/2010 |
| KR | 20-0425370 | 9/2006 |
| RU | 2218895 | 12/2003 |
| WO | 2007/124537 | 11/2007 |
| WO | WO 2008153263 A1 * | 12/2008 |

OTHER PUBLICATIONS

Boenisch M., M.D., "Healing process of cartilage attached to a polydioxanone implant". HNO., Oct. 2000 (2). ,48(10):743-6.

Boenisch M., MD., "Influence of Polydioxanone Foil on Growing Sepal Cartilage After Surgery in an Animal Model", Archives of Facial Plastic Surgery, Jul./Aug. 2003. vol. 5.

F. Watzinger et al., "Biodegradable polymer membrane used as septal splint",Int. J. Oral Maxillofac. Surg. 2008; 37: 473-477.

Kal Ansari, MD, FRCSC, "Grafts and implants in rhinoplasty—Techniques and long-term results", Operative Techniques in Otolaryngology (2008) 19, 42-58.

Samuel Stal, M.D. et al, "The Use of Resorbable Spacers for Nasal Spreader Grafts", Plastic and Reconstructive Surgery, Sep. 2000, vol. 106, No. 4, pp. 922-923.

Wolfgang Gubisch, MD, "Extracorporeal Septoplasty for the Markedly Deviated Spectum", Archives of Facial Plastic Surgery, Jul./Aug. 2005, vol. 7.

"LactoSorb Grafting for Cartilage Preservation in Rhinoplasty" Barry Eppley http://exploreplasticsurgery.com/2008/06/29/lactosorb-grafting-for-cartilage-preservation-in-rhinoplasty/.

"LactoSorb®: The Proven Leader in Resorbable Technology" (http://www.lorenzsurgical.com/category.php?cat=5.

International Preliminary Report on Patentability re: PCT/US2012/025614 dated Aug. 21, 2013.

International Search Report re: PCT/US2012/025614 dated Jun. 4, 2012.

Echeverry, A. MD et al "Alternative Technique for Tip Support in Secondary Rhinoplasty" Aesthetic Surgery Journal—Nov./Dec. 2006 26(6) pp. 662-668.

James, S.E. (Plast.) et al "Cartilage Recycling in Rhinoplasty: Polydioxanone Foil as an Absorbable Biomechinal Scaffold", Plastic and Reconstructive Surgery Jul. 2008, vol. 122, No. 1, pp. 254-260.

Kim, Y.O. et al, "Aesthetic reconstruction of the nasal tip using a folded composite graft from the ear", The British Association of Plastic Surgeons (2004) 57, pp. 238-244.

Lawson, W. et al, "The Silicone Columellar Strut", Plastic and Reconstructive Surgery, Apr. 1996 vol. 97(5) Supplement pp. 938-943.

Lovice, D.B. et al, "Grafts and Implants in Rhinoplasty and Nasal Reconstruction" Otolaryngologic Clinics of North America (1999) 32(1) pp. 113-141.

Romo, T. III, et al "Nasal Grafts and Implants in Revision Rhinoplasty" Facial Plast Surg Clin N Am (2006) 14 pp. 373-387.

Romo, T. III, et al, "Nasal Implants", Facial Plast Surg Clin N Am (2008) 16 pp. 123-132.

Toriumi, D. "New Concepts in Nasal Tip Contouring", Archives of Facial Plastic Surgery, vol. 8 May/Jun. 2006, pp. 156-185.

http://www.hansonmedical.com/nasal.html (2010) 2 pages.

http://www.porexsurgical.com/english/surgical/snasaldartt.asp MEDPOR® Nasal DARTT Implant (2010) 1 page.

International Preliminary Report on Patentability re: PCT/US2011/053242 dated Apr. 2, 2013.

International Search Report re: PCT/2011/053242 dated Dec. 6, 2011.

International Search Report re: PCT/US2013/042144 dated Aug. 5, 2013.

Written Opinion re: PCT/US2013/042144 dated Aug. 5, 2013.

International Preliminary Report re: PCT/US2013/042144 dated Nov. 25, 2014.

* cited by examiner

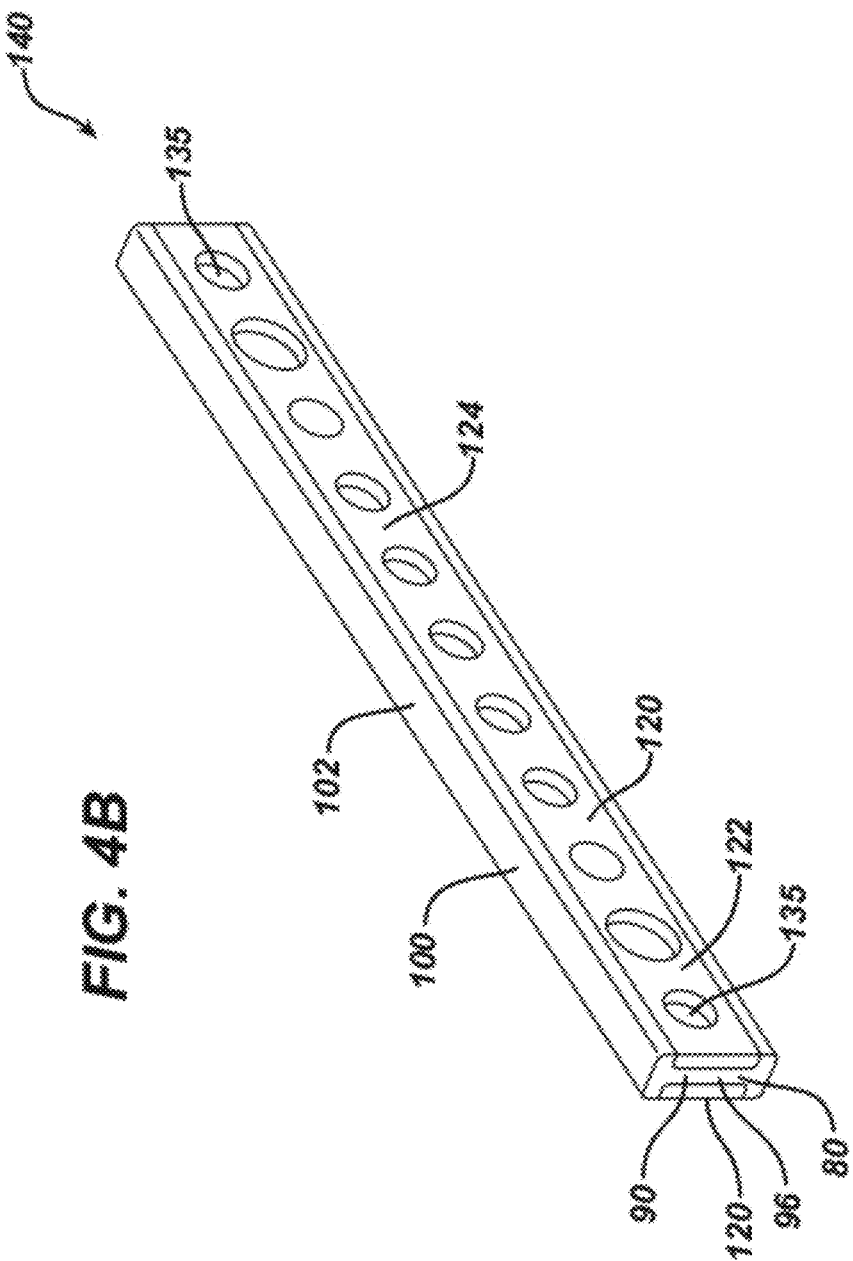

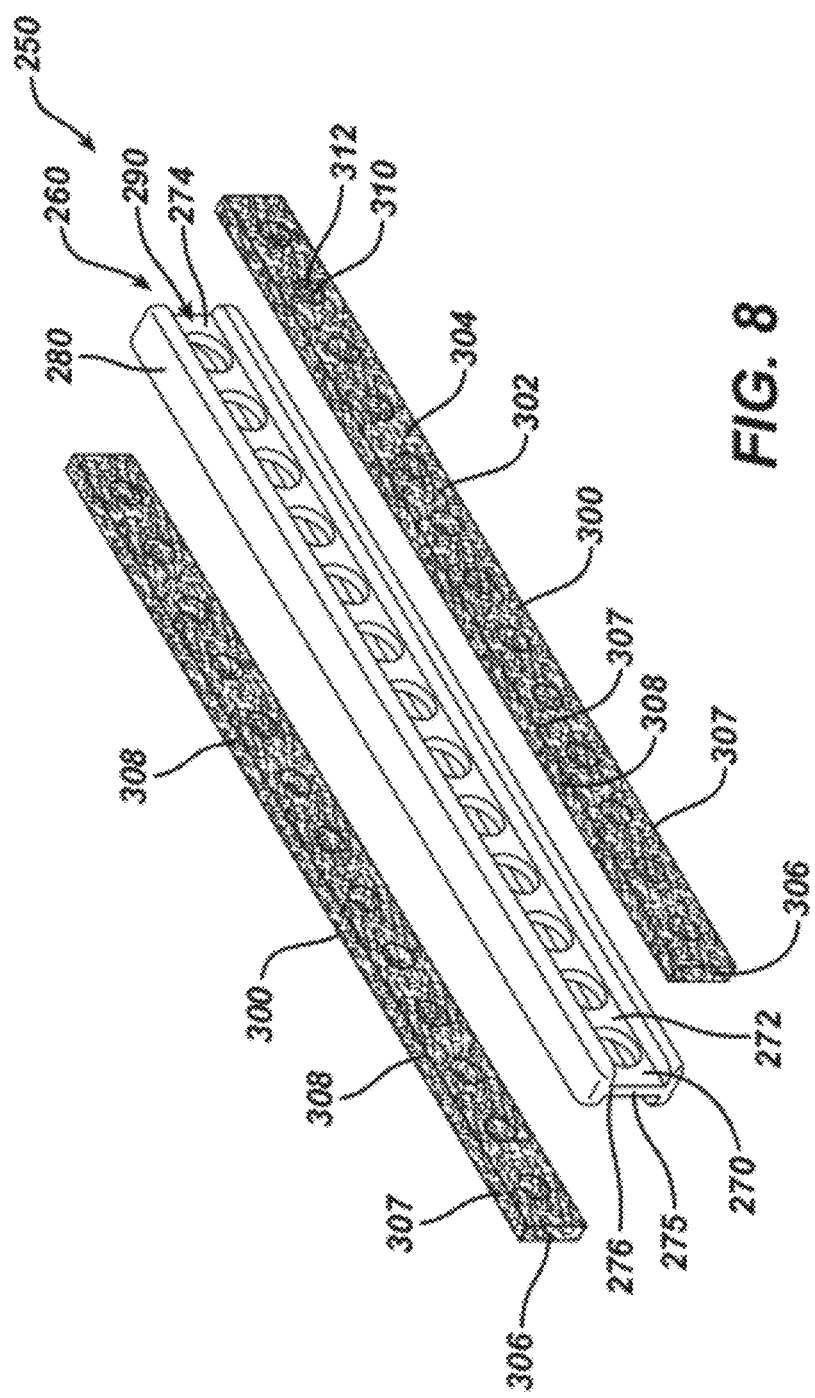

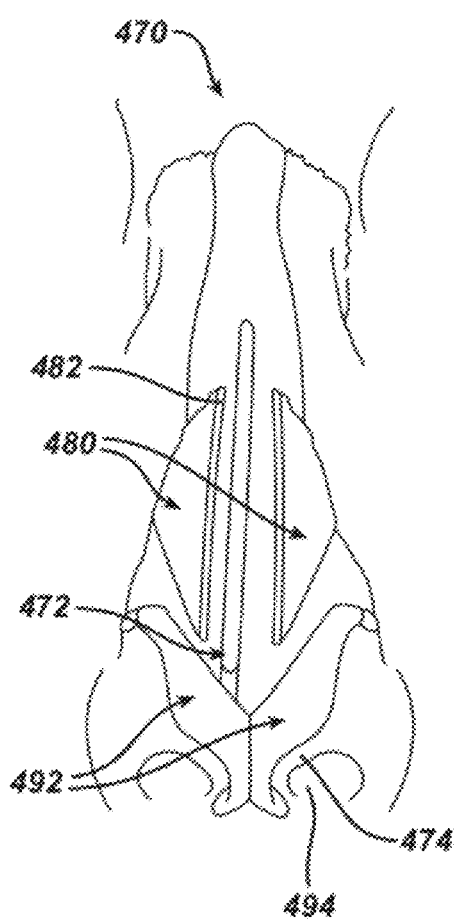
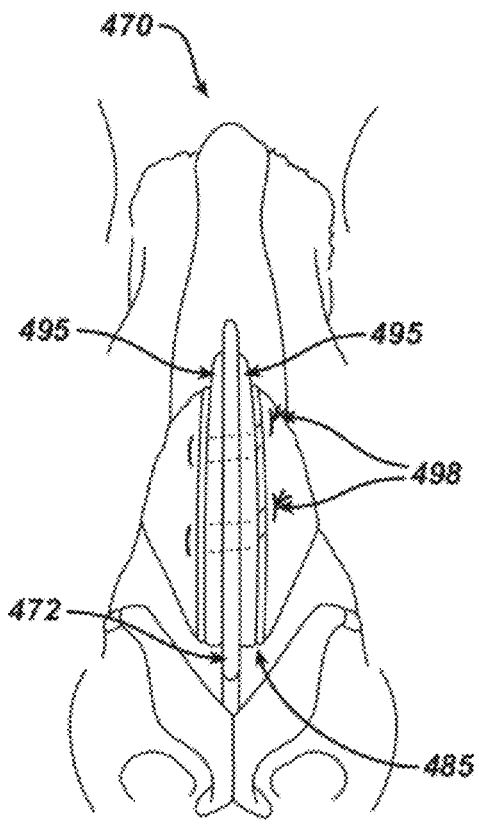

BIOABSORBABLE MULTILAYER NASAL VALVE SPREADER GRAFT

FIELD OF THE INVENTION

The field of art to which this invention relates is bioabsorbable implantable medical devices, in particular, bioabsorbable implantable medical devices for use in nasal aesthetic and reconstructive surgical procedures.

BACKGROUND OF THE INVENTION

The human nose is a relatively complex structure that allows for the inhalation of air and exhalation of air and carbon dioxide and other cellular waste products. The nose also accomplishes physiological functions including humidification, temperature control and filtration of the inspired air. The nose additionally is a sensory organ responsible for the olfactory sense. For most people, the nose performs these functions efficiently and relatively trouble-free. However, patients often complain of symptoms relating to restricted airflow in their nasal passages. The septal cartilage structure of the nose divides the nose into two passages. These passages are typically described or referred to as nostrils. Inspired air moves through the nostrils, the nasal vault, and the nasopharyngeal wall, the pharynx, larynx, trachea, bronchi and reaches the alveoli in lungs. Inhalation and exhalation are responsive to movement of the diaphragm and the intercostal muscles of the ribs. It is estimated that more than 50% of the total respiratory resistance of the respiratory tract occurs in the nose. It is known that airway obstruction may be attributable to various factors, including deviated septum, suboptimal position and rigidity of the lateral nasal walls, etc. The internal nasal valve is described as the space between the fold of the upper lateral cartilage (ULC) and the nasal septum. The angle between the septum and the upper lateral cartilage normally ranges between 10 and 15 degrees. It is generally accepted that nasal resistance behaves in accordance with Poiseuille's law and Bernoulli's principle, which means that small changes in the nasal valve area have an exponential effect on the airflow. Patients with less than a 10 degree angle at the internal nasal valve usually have airflow obstruction and are diagnosed with internal valve stenosis. The internal nasal valve may also be narrowed due to thickening of the septum or by a deviated septum. Additional causes of nasal obstruction include trauma to the nose, face or head, burns, and elective surgery. Surgery of the nose involves repositioning of the nose's bony and cartilaginous structures. Excessive scarring due to aggressive resection may also lead to resultant narrowing of the nasal valve area. The internal valve may also become collapsed due to poor cartilage quality or position. As the internal valve collapses, the airflow becomes obstructed. The external nasal valve is composed of the nasal ala and supporting structures of the lower lateral cartilages.

These areas are named valves because they regulate the cross-sectional area of the nasal airway and perform dynamic functions. The collapse of the lateral nasal walls at the internal valve is known to be associated with a reduction rhinoplasty procedure commonly referred to as 'hump removal'. During such reduction rhinoplasty, a hump in the cartilaginous and/or bony dorsum of the nose needs to be resected, which leads to reduction of the overall valve area and destabilizing of the ULC. The patient may experience post-surgical breathing problems if the nasal valve is not properly repaired after this procedure. This nasal valve reconstruction is typically done by the surgeon emplacing unilateral or bi-lateral spreader grafts on the nasal septum from the cephalic to the caudal portion of the nasal septum. Such devices and procedures widen the cross-sectional area of the upper nasal valve. However, there are deficiencies present in and associated with the use of conventional spreader grafts, which are typically made from autologous cartilage. The deficiencies include the need for autologous cartilage harvesting resulting in donor site morbidity, and increased pain and duration of the procedure. Although non-absorbable spreader graft implants exist, surgeons prefer not to use them due to the increase risk of complications such as infection and extrusion.

Therefore, there is a need in this art for novel bioabsorbable, multilayer spreader grafts for nasal reconstruction procedures that increase the spacing between nasal upper lateral cartilages without using permanent foreign body material to achieve permanent repositioning of the upper lateral cartilages and which provide improved structural support in patients undergoing plastic or reconstructive surgical nasal procedures. There is also a need for novel bioabsorbable spreader grafts which promote tissue ingrowth and minimize long term complications, and which are relatively easy for the surgeon to implant, and which further provide a superior result for the patient.

SUMMARY OF THE INVENTION

Accordingly, novel bioabsorbable nasal valve spreader graft devices are disclosed. In a first embodiment, the bioabsorbable, nasal valve spreader device has an elongated core plate member having first and second opposed lateral sides. The lateral sides have outer surfaces. The core plate member has an outer periphery, opposed ends, and a plurality of openings including at least one engagement opening extending through the plate member. An optional flange member extends about at least part of the periphery of the core plate member forming a cavity above the outer surface of each lateral side. The device has at least one elongated spreader plate member having first and second opposed lateral sides with at least one snapping pin member extending from at least one lateral side. There is a plurality of openings extending through the spreader or expansion plate. The core and spreader plate members are secured to each other by engaging the at least one snapping pin member in an engagement opening in the core plate. The devices are made from a bioabsorbable polymer. The device may optionally consist of two or more spreader plate members.

Yet another aspect of the present invention is a novel bioabsorbable nasal valve spreader graft device having tissue ingrowth substrates. The bioabsorbable, nasal valve spreader implant device, has an elongated core plate member having first and second opposed lateral sides. The lateral sides have outer surfaces. The core plate member has opposed ends, an outer periphery, and a plurality of openings extending through the plate member. A flange member extends about at least part of the periphery of the core plate member forming a cavity above the outer surface of each lateral side. The device has an elongated tissue ingrowth plate member having first and second opposed lateral sides, and a plurality of openings extending through said second ingrowth plate member. The ingrowth plate member is mounted to the core plate member by inserting the ingrowth plate member at least partially into the cavity on one side of the core plate member. A tissue ingrowth plate member may be mounted in both cavities. Optionally, the tissue ingrowth member does not contain openings extending therethrough.

Another aspect of the present invention is a method of performing a surgical procedure using the above-described bioabsorbable nasal valve spreader graft devices.

These and other aspects and advantages of the present invention will be more apparent from the following description and accompanying drawings.

BRIEF DESCRIPTION OF THE DRAWINGS

FIG. 8 is an exploded perspective view of an additional alternate embodiment of a spreader graft implant device of the present invention having an I-beam core plate member and tissue ingrowth plates; the I-beam core plate member is seen to have open ends.

FIGS. 13A and 13B are anatomic schematic diagrams illustrating an internal nasal valve having a deviated septum, and the septum after correction using a nasal spreader graft implant of the present invention.

DETAILED DESCRIPTION OF THE INVENTION

Figure 1:
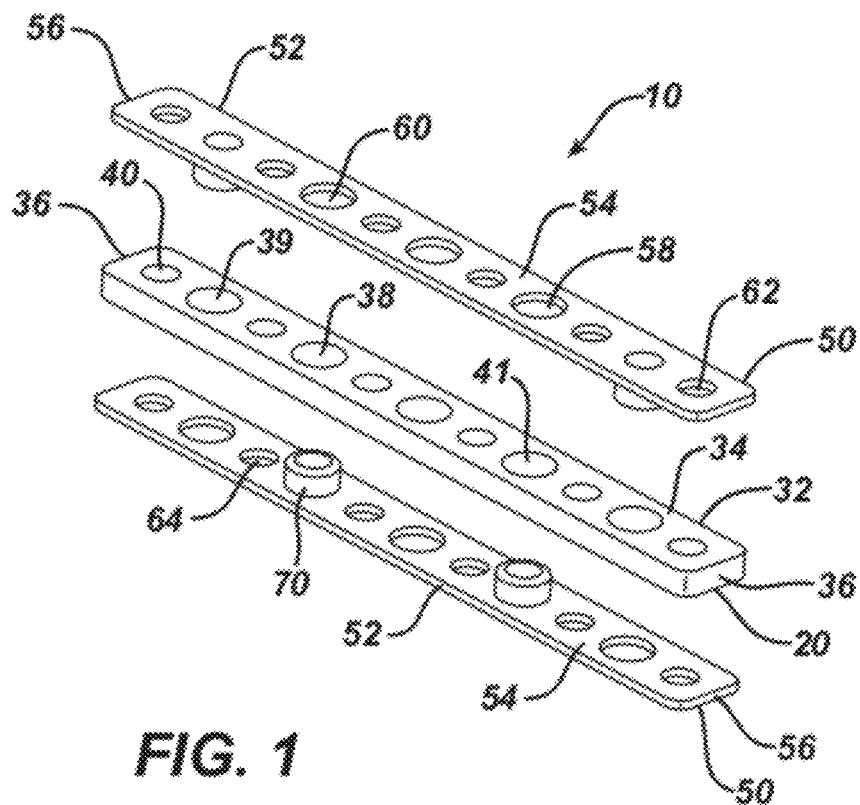
FIG. 1 is an exploded perspective view of a nasal spreader graft device of the present invention having two spreader plate members.

The novel, bioabsorbable graft spreader devices of the present invention are made from conventionally known bioabsorbable polymers and equivalents thereof. The bioabsorbable polymers useful to manufacture the nasal graft spreader devices of the present invention will have several desirable properties, including good initial strength and breaking strength retention (BSR) and predictable bioabsorption, for example after implantation for a period of 6-20 weeks, and essentially complete bioabsorption in about 6-12 months. However other strength and absorption profiles may be designed for a particular application. Particularly suitable polymers may include conventional bioabsorbable polymers such as poly(p-dioxanone), poly(glycolide-co-lactide) with lactide-rich copolymers (e.g. 70%-90% lactide), or their blends thereof, etc. Suitable absorbable polymers may be synthetic or natural polymers. Suitable biocompatible, bioabsorbable polymers include aliphatic polyesters, poly (amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue. The spreader graft devices of the present invention will preferably be made from the following bioabsorbable polymers: poly(p-dioxanone), co-polymers of poly(lactide-co-glycolide), and the blends thereof.

The term BSR or Breaking Strength retention as used herein is defined to have its conventional meaning, i.e., the breaking strength remaining in the device after a certain period of incubation in vivo or in vitro under a given set of conditions. The term bioabsorbable polymer as used herein is similarly defined to have its conventional meaning, i.e., polymer molecules that can degrade as a result of hydrolysis or interaction with the body fluid, and eventually be absorbed and/or excreted completely by the body after a certain period of time.

Particularly suitable polymers may include conventional bioabsorbable polymers including poly(p-dioxanone), poly(glycolide-co-lactide) with lactide-rich copolymers (e.g. 70-90% lactide), and blends thereof, etc. Bioabsorbable polymers useful in the devices of the present invention may include polymers selected from biobsorbable aliphatic polyesters. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue.

The devices of the present invention can be made using conventional manufacturing processes including compression forming, injection molding, thermoforming, profile extrusion, and the like. The devices of the present invention may be optionally coated or bonded with various conventional materials including absorbable polymers, biologics, therapeutic agents, absorbable fibers, combinations thereof and the like using conventional coating or bonding processes. For example, coatings may be deposited on the surfaces by various conventionally known methods including spraying, dipping, immersion, lamination, electrostatic and the like. A bonded thin layer of non-woven absorbable material applied to the devices of the present invention, for example, melt-blown poly(p-dioxanone) nonwoven or a coating, can provide faster tissue ingrowth and more comfort to the patient. The coating materials may comprise therapeutic or active agents such as pharmacologically and/or biologically active agents, including, but not limited to, antibacterial agents, antimicrobial agents, growth factors, and wound healing agents. Active agents may include conventional therapeutic agents for the treatment of pain and/or prevention of infection. Examples of active ingredients may include non-steroid anti-inflammatory drugs (NSAIDs) such as diclofenac sodium, indomethacine, ketoprofen etc. Other types of active agents suitable to this invention may include conventional antibacterial agents such as triclosan and antibiotics.

Additionally, the devices of the present invention may be made from a bioabsorbable semi-rigid foam structure. The foam preferably has open and inter-connected pores, although it may also have closed pores. The absorbable foam may be formed by any conventional method. For example, a gas or gas-forming agent may be added to absorbable polymer during or before being extruded to form a foam sheet. A water-soluble agent such as a salt may also be blended with an absorbable polymer to form a solid sheet first.

Conventional lyophylization processes may also be used to form the material used to construct the spreader graft devices of the present invention. Those skilled in the art will appreciate that certain of the previously mentioned bioabsorbable polymers may be more useful to form foam structures than others, depending upon their individual characteristics that make them useful in a foam forming process and the desired mechanical characteristics of the device. Some of the polymers that are useful to form foamed structures include poly(p-dioxanone), co-polymers of poly(lactide-co-glycolide) and the blends thereof.

One or more surfaces of the devices of the present invention may optionally have a specific surface roughness to facilitate fixation by increased friction and to create more favorable conditions for cell migration. The surface treatment can be provided in a variety of conventional manners, for example, during injection molding via the mold surfaces or in a surface blasting process similar to sand-blasting. Optionally, micro pores or perforations of about 50-500 µm may be added throughout the surfaces to promote nutrition passage and tissue ingrowth.

Figure 2:
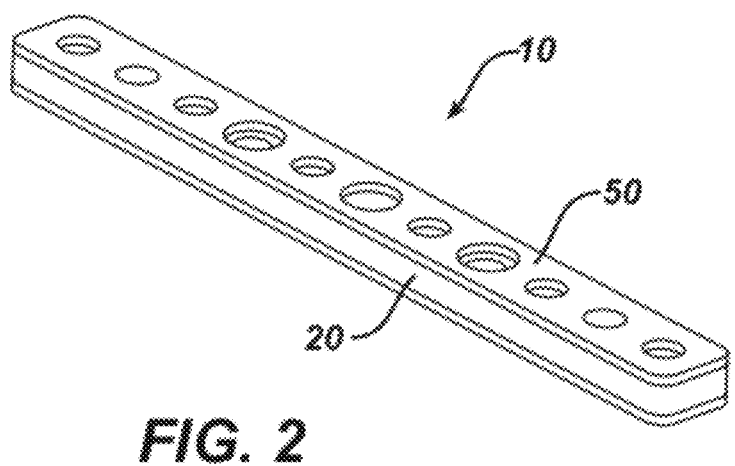
FIG. 2 is a perspective view of the spreader graft device of FIG. 1 in an assembled configuration.
Figure 3A:
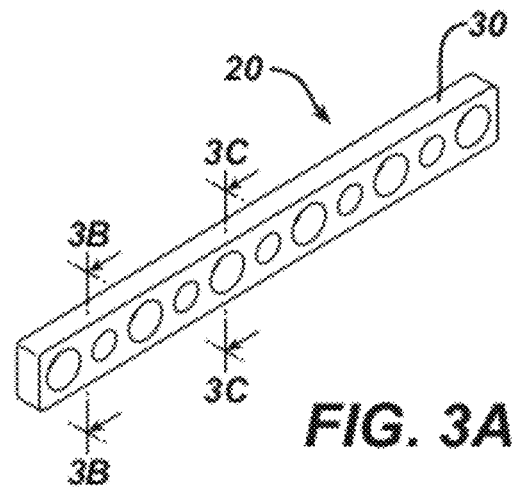
FIGS. 3A-C illustrate a perspective view of the core plate member of the graft device of FIG. 1, along with two cross-sectional views.
Figure 3B:
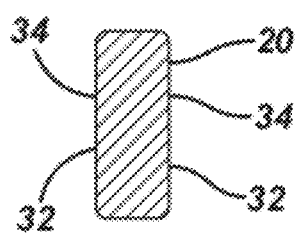
Figure 3C:
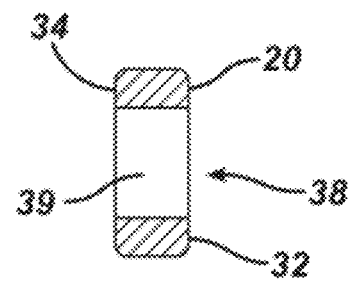

A nasal graft spreader device 10 of the present invention is illustrated in FIGS. 1-3. The device 10 is seen to have core plate member 20 and a spreader plate member 50. Core plate member 20 is seen to be an elongated core plate 30 having opposed lateral sides 32 with outer surfaces 34. The plate 30 is also seen to have opposed ends 36. The core plate 30 is seen to have at least one engagement or engaging opening 38 on each side 32 having passage 39 extending therethrough and at least one suture opening 40 on each side 32 having passage 41 extending therethrough. The openings 38 and 40 preferably have a circular configuration, but may have other geometric configurations including but not limited to oval, semi-circular, square, triangular, polygonal, and combinations thereof. The device 10 of the present invention also has at least one removable and engageable spreader plate member 50. Plate member 50 is seen to be a flat, elongated plate member having opposed lateral sides 52, opposed ends 56, and outer surfaces 54 on sides 52. The plate members 50 are seen to have first pin engagement openings 58 with passages 60 extending therethrough and second suture openings 62 with passages 64 extending therethrough. The plate members are seen to have snapping pins 70 extending from at least one surface 54. The snapping pins 70 are seen to be substantially cylindrically shaped, but may have other shapes including oval, semi-circular, square, triangular and combinations thereof. The pins 70 are designed to engage with the engagement openings 38 of the core plate 30, and the shape of the pins 70 is dictated by the shape of the engagement openings 38 to provide for mechanical engagement of the pins 70 in the openings 38 and passages 39. Such engagement may be described as a mechanical force fit or interference fit. If desired, other conventional locking structures may be used. The device 10 is assembled by mounting one or more spreader plate members 50 to the core plate member 20. The number of spreader plate members 50 utilized will be determined by the surgeon and will depend upon a number of factors such as the natural size of the nose, the level of deformity of the nasal valve or septum, etc. Depending upon the surgical need, one or multiple spreader plates 50 may be stacked together to obtain the appropriate thickness, such that engagement pins 70 of one plate member 50 are engaged by engagement openings 58 of another spreader plate member 50. The spreader plates 50 may be different thicknesses. The suture openings 40 and passages 41 are present to receive sutures or other fastening devices during an emplacement surgical procedure, as are the suture openings 62 and passages 64. When assembled, the openings 40 and passages 41 of core plate 30 will align with openings 62 and passages 64 of spreader plate members 50. Although not illustrated, the spreader plates may be pre-assembled by mounting two or more spreader plates 50 together utilizing the mounting pins 70 and engagement openings 58, prior to mounting the pre-assembly to a core plate member 50. Also not illustrated, but within the scope of the present invention, is an embodiment of the core plate member optionally having snapping pin members extending from the outer surfaces 34 to engage the engagement openings 58 of a spreader plate member 50.

Another embodiment of a nasal graft spreader device 140 of the present invention having a core plate member 80 with an I-beam configuration is illustrated in FIGS. 4A-F. The core plate member 80 is seen to have an elongated core plate 90 having opposed lateral sides 92 and opposed ends 96. The core plate 90 is seen to have outer surfaces 94. The core plate member 80 has a flange member 100 extending out from the outer periphery 98 of the plate 90. The outer periphery 98 is defined by the opposed lateral edges 97 of core plate 90 Flange 100 is seen to have top side 102 and inner sides 104. The core plate is seen to have engagement openings 106 having passages 107 extending therethrough, and suture openings 108 having passages 109 extending therethrough. The flange member inner surfaces 104 and the core plate surfaces 94 form cavities 110 on either side of plate 90 for receiving spreader plate members 120 having engagement pins 135. The spreader plate members 120 are seen to be elongated plate members. Plate member 120 is seen to be a flat, elongated plate member having opposed lateral sides 122, opposed ends 126, and outer surfaces 124 on sides 122. The plate members 120 are seen to have first pin engagement openings 128 with passages 130 extending therethrough, and second suture openings 132 with passages 134 extending therethrough.

Figure 4A:
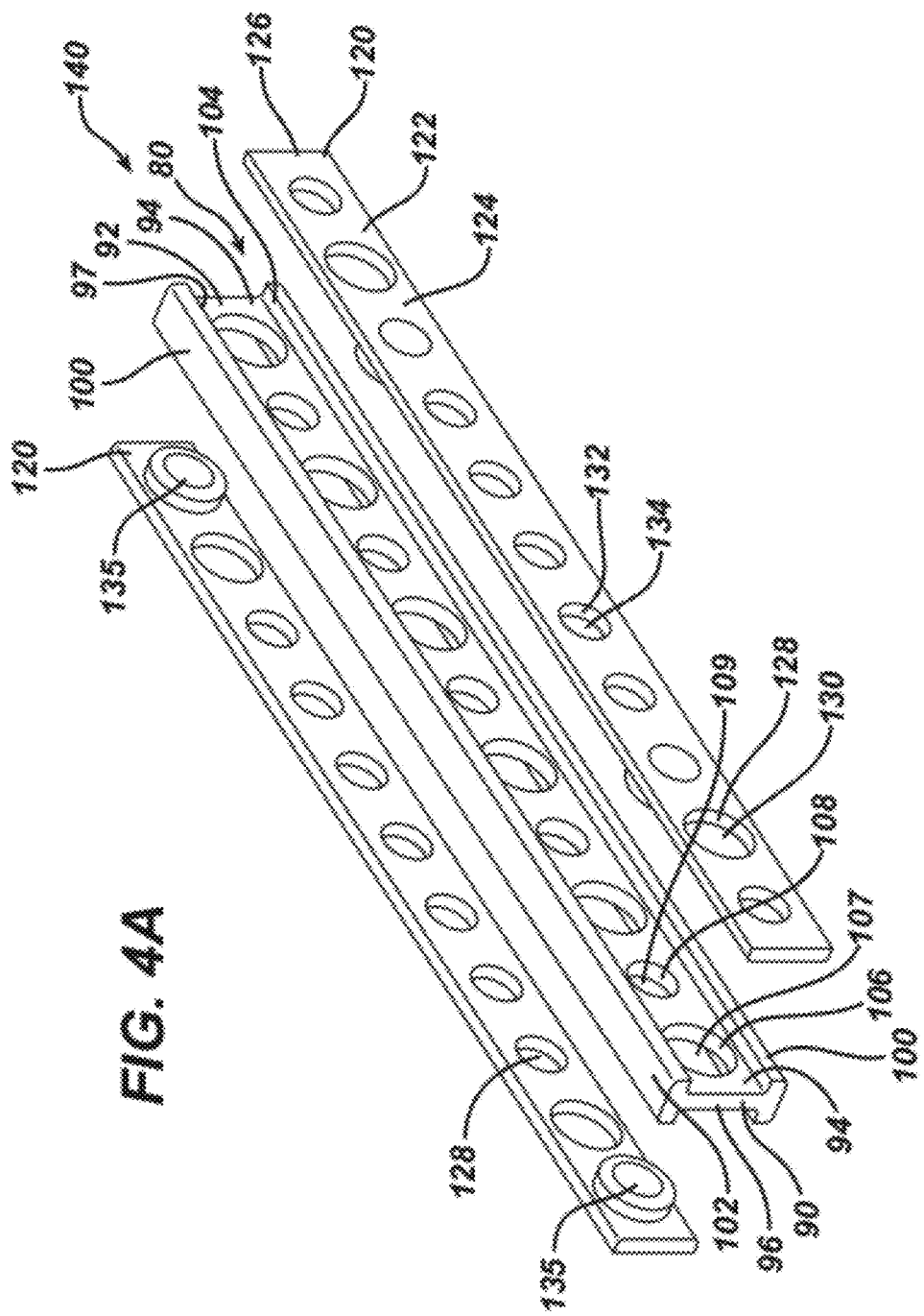
FIG. 4A is an exploded perspective view of an alternative embodiment of a nasal spreader graft device of the present invention, wherein the core plate member has an I-beam configuration.
Figure 4C:
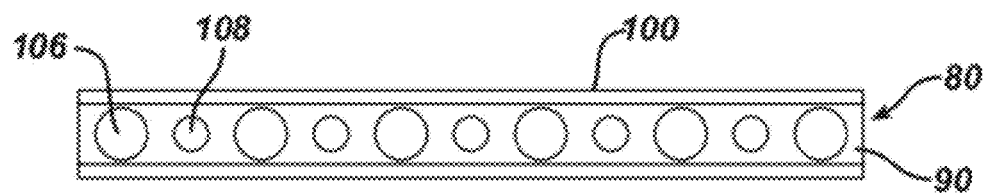
FIG. 4B is a perspective view of the spreader graft device of FIG. 4A in an assembled configuration.
FIG. 4 C is a side view of the core plate member of the device of FIG. 4A.
FIG. 4D is a cross-sectional view of the core plate member of FIG. 4E.
FIG. 4E is a perspective view of the core plate member of FIG. 4A.
FIG. 4F is a cross-sectional view of the core plate member of FIG. 4E.
Figure 4E:
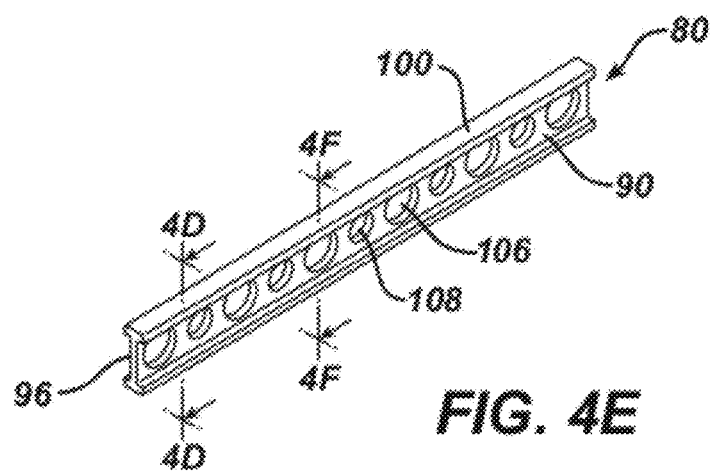
Figure 4D:
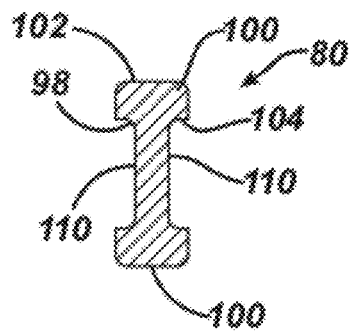
Figure 4F:
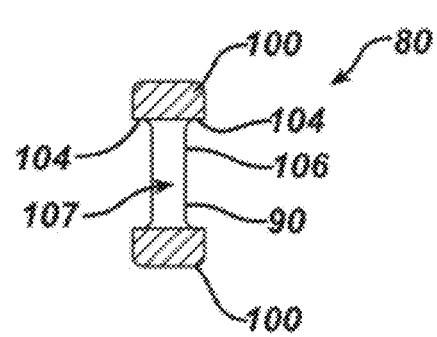

The spreader plate members 120 are seen to have snapping pins 135 extending from at least one surface 124. The snapping pins 135 are seen to be substantially cylindrically shaped, but may have other shapes including oval, semicircular, square, triangular, and combinations thereof. The pins 135 are designed to engage with the engagement openings 106 of the core plate 90, and the shape of the pins 120 is dictated by the shape of the engagement openings 106 to provide for mechanical engagement of the pins 135 in the openings 106 and passages 107. Such engagement may be described as a mechanical force fit or interference fit. The device 140 is assembled by mounting one or more spreader plate members 120 to the core plate member 80 such that the pins 135 are engaged in openings 106 and passages 107 and spreader plate members 120 are at least partially contained in cavities 110. When assembling a device 140 of the present invention as seen in FIGS. 4A and 4B, the spreader plate members 90 are mounted to the core plate member 80 in a similar manner as described above for device 10. The plate members 120 will be at least partially contained in cavities 110 after assembly to form the device 140. If desired, additional spreader plate members 120 may be mounted to an assembled device 140 by mounting additional spreader plate members 120 having offset pins 135 and engaging openings 128 and passages 130 of the previously mounted plate members 120 with the pins 135.

Another embodiment of a spreader graft device 150 of the present invention is seen in FIG. 5, FIGS. 6A-C, and FIGS. 7A-C. The device 150 is seen to have a central core plate member 160. Core plate member 160 is seen to have elongated core plate 170 having opposed lateral sides 172 with outer surfaces 174. The core plate 170 has opposed rounded ends 176, however the ends 176 may have other configurations including straight, pointed, angulated, and the like. The core plate is also seen to have outer periphery 177, and suture openings 178 with passages 179. The core plate 170 is seen to have a flange member 180 extending about the periphery 177 of core plate 170, thereby forming cavities 190 on top of surfaces 174. Flange member 180 is seen to have opposed sides 182, inner surfaces 184 and outer surface 186. Cavities 190 are bounded by surfaces 184 and surfaces 174. The spreader graft device 150 is also seen to include tissue ingrowth plates 200. The tissue ingrowth plates 200 are elongated members having opposed lateral sides 202 having surfaces 204. The plates 200 have rounded opposed ends 206, however the ends 206 will be configured to match the ends 176 of core plate 170. Each plate 200 is seen to have an outer periphery 208. Plates 200 also have suture openings 210 having passages 212. The openings 210 are preferably in alignment with the suture openings 178 of core plate 170. In another embodiment of the present invention, the tissue ingrowth plates do not have openings for sutures. The device 150 is assembled by inserting the plates 200 into the cavities 190 on the opposed sides 172. The plates 200 may be partially contained in cavities 190 or completely contained therein. The plates 200 are typically affixed or engaged in cavities 190 by a mechanical or force fit, but may also be affixed or engaged by other conventional means including biocompatible glues and adhesives, welding, mechanical fixation devices, and the like. The plates 200 are constructed of a biocompatible biodegradable material that promotes tissue ingrowth. Examples of such materials include nonwoven fabrics, foams, woven fabrics, knitted meshes, porous or perforated plates and the like.

Another embodiment of a nasal graft spreader device 250 of the present invention is illustrated in FIGS. 8, 9A-C, and 10A-C. The device 250 is seen to have a central core plate member 260. Core plate member 260 is seen to have elongated core plate 270 having opposed lateral sides 272 with outer surfaces 274. The core plate 270 has opposed 90° straight or squared ends 275, however the ends 275 may have other configurations including rounded, pointed, angulated, and the like. The core plate is also seen to have outer lateral edges 276 and outer periphery 277, and suture openings 278 with passages 279. The core plate 270 is seen to have top and bottom flange members 280 extending about the periphery 277 of core plate 270 along lateral edges 276, thereby forming cavities 290 on top of surfaces 274. Flange members 280 are seen to have opposed sides 282, inner surfaces 284 and outer surfaces 286. Cavities 290 are bounded by surfaces 284 and surfaces 274. Depending on the number of flanges (1 or 2), relative width of the flanges, and/or relative position of the flanges 280 to the central core plate 270, the cross-section of the core plate member 260 may take the shape (i.e., cross-section) of an I, L, H or inverted or upright T, or referred to as an I-beam cross-section, an L-beam cross-section, an H-beam cross-section, and a T-beam cross-section. The spreader graft device 250 is also seen to include tissue ingrowth plates 300. The tissue ingrowth plates 300 are elongated members having opposed lateral sides 302 having surfaces 304. The plates 300 have straight or squared 90° opposed ends 306. However, the ends 306 will preferably be configured to match the ends 276 of core plate 270. Each plate 300 is seen to have outer periphery 307 and outer surface 308. Plates 300 also have suture openings 310 having passages 312. The openings 310 are preferably in alignment with the suture openings 278 of core plate 270. In another embodiment of the present invention, the tissue ingrowth plates do not have openings for sutures. The device 250 is assembled by inserting the plates 300 into the cavities 290 on the opposed sides 272. The plates 300 may be partially contained in cavities 290 or completely contained therein. The plates 300 are typically affixed or engaged in cavities 290 by a mechanical or force fit, but may also be affixed or engaged by other conventional means including biocompatible glues and adhesives, welding, mechanical fixation devices, and the like. The plates 300 are constructed of a biocompatible biodegradable material that promotes tissue ingrowth. Examples of such materials include nonwoven fabrics, foams, woven fabrics, knitted meshes, porous or perforated plates and the like.

There can be additional embodiments and variations of the nasal spreader graft devices within the scope and contemplation of the present invention, including having the tissue ingrowth plate inserted in the center of the device. For example, the spreader graft device implant may consist of a mini-case core plate and a nonwoven (NW) ingrowth member which may be inserted into the central cavity of the mini-case core plate. The mini-case may look like a small elongated box having a central cavity for the insertion of cartilage or tissue ingrowth NW. The porous NW insert can be used "as is" or padded with autologous or other cartilage scraps or tissue grafts. The NW insert may also be removed and replaced completely with cartilage or cartilage scraps or tissue grafts if so desired. The mini-case may be closed with a snap-on means or in situ while the device is fixated to or about the implanting site. Also contemplated are combinations of both spreader plates and tissue ingrowth plates with core plate members.

The thickness of spreader graft devices of the present invention used to increase spacing between nasal upper lateral cartilages (ULC) is sufficient to provide effective spacing and correction, typically in the range of about 1.5 mm to about 3.0 mm. A spreader graft made from a single layer of a polymeric plate could be difficult to cut to different length or shapes. By having a multiple layer structure, the thickness of the individual layers can be maintained relatively thin, preferably equal or less than about 1.5 mm. A polymeric plate of thickness of less than 1.5 mm is easier to trim without the need to use a high temperature bath to soften the structure at the time of the surgery. The widths and lengths of the spreader graft devices of the present invention will be sufficient to effectively support the internal nasal valve and increase the width of the middle nasal vault. The length of the spreader graft devices will typically range from about 35 mm to about 45 mm, while the widths will typically range from about 1 mm to about 2 mm. However, it will be appreciated by those skilled in the art that a variety of different widths, lengths and thicknesses may be employed in the spreader grafts of the present invention depending upon a number of variables including but not limited to the procedural application and materials of construction.

Variable overall thicknesses of the spreader grafts of the present invention may be obtained by the surgeon selecting different combination of layers to meet different needs in different situations. The thicknesses of the core plates and spreader plates and tissue ingrowth plates of the spreader graft devices will be sufficient to provide effective correction and opening to the nasal defect. Several plates of different thickness may be supplied in a package or a device "kit". Surgeons may readily assemble them in situ by snapping two or more layers together. The core plate members of the implantable graft may typically have a thickness of about 1.0 to about 1.5 mm and the spreader plates may typically have a thickness in the range of about 0.2 mm to about 0.5 mm, and any optional additional add-on plates may have thicknesses typically in the range of about 0.2 to about 1.0 mm.

In various embodiments of the spreader graft devices of the present invention, the spreader graft device may have a variable overall thickness and/or width along the length of the device. For example, the device may taper from the proximal to the distal end, both ends may be tapered, the device may taper from the ends toward the center, etc. Other embodiments having varying dimensions include alternating segments along the length of the device having, for example, different widths, thicknesses, etc. This can be accomplished by varying the dimensions of some or all of the various components of the nasal spreader graft devices. For example the flanges may be tapered or have varying thicknesses or widths, the core plate may be tapered and have varying thicknesses and widths, and the spreader plate members and tissue ingrowth plates may similarly be tapered and have varying thicknesses and widths.

The core plate member and add-on layers or spreader plates may be made from the same absorbable polymer. However, it may be desirable to have different absorption profiles from the spreader plates or tissue ingrowth plates to the core so that the device does not lose structural integrity suddenly due to bulk degradation. It is preferable for the outer layers to degrade faster, allowing tissue to grow inside the pores or around the fragments after partial degradation of the spreader plate or tissue ingrowth plate layers. The core plate member should provide sufficiently effective support in vivo, for example, typically about 10 weeks, preferably for more than about 20 weeks, until sufficient tissues are formed inside or in replacement of the outer layers, although other time periods may be utilized depending upon the application and procedure. It is preferable for the core plate member to be essentially absorbed within about 10 to about 12 months.

To further facilitate or speed up the tissue in-growth process after surgery, it may be advantageous to have pre-existing pores in the outer layers of the spreader graft device (i.e., spreader plates and tissue ingrowth plates). This allows the cells to readily migrate and grow inside the pores immediately or shortly after the surgery. For example and as described herein, the porous outer layers may be constructed from bioabsorbable nonwoven materials. The nonwoven layers or plates may have the same or different absorption profiles. The core plates and core plate members are preferably made from a solid plate, which provides strong and prolonged structural support to maintain desirable opening of nasal valves during healing until sufficient tissue has grown in the outer layers of the implant, but if desired may also be made from porous nonwoven materials.

The nonwoven materials typically will have the following characteristics: fiber diameter in the range of about 1 to about 25 $\mu m$, pore sizes of about 1 $\mu m$ to about 50 $\mu m$, a porosity of about 10% to about 90%, and a mass density of about 20 grams per square meter to about 250 grams per square meter. Those skilled in the art that other ranges of these parameters may be utilized depending upon a number of factors including mechanical structure, polymers utilized, desired in vivo characteristics, etc. The nonwoven structure of a high porosity with interconnected pores allows tissue cells to migrate readily and serves as scaffold for tissue ingrowth immediately following the completion of surgery.

Figure 11:
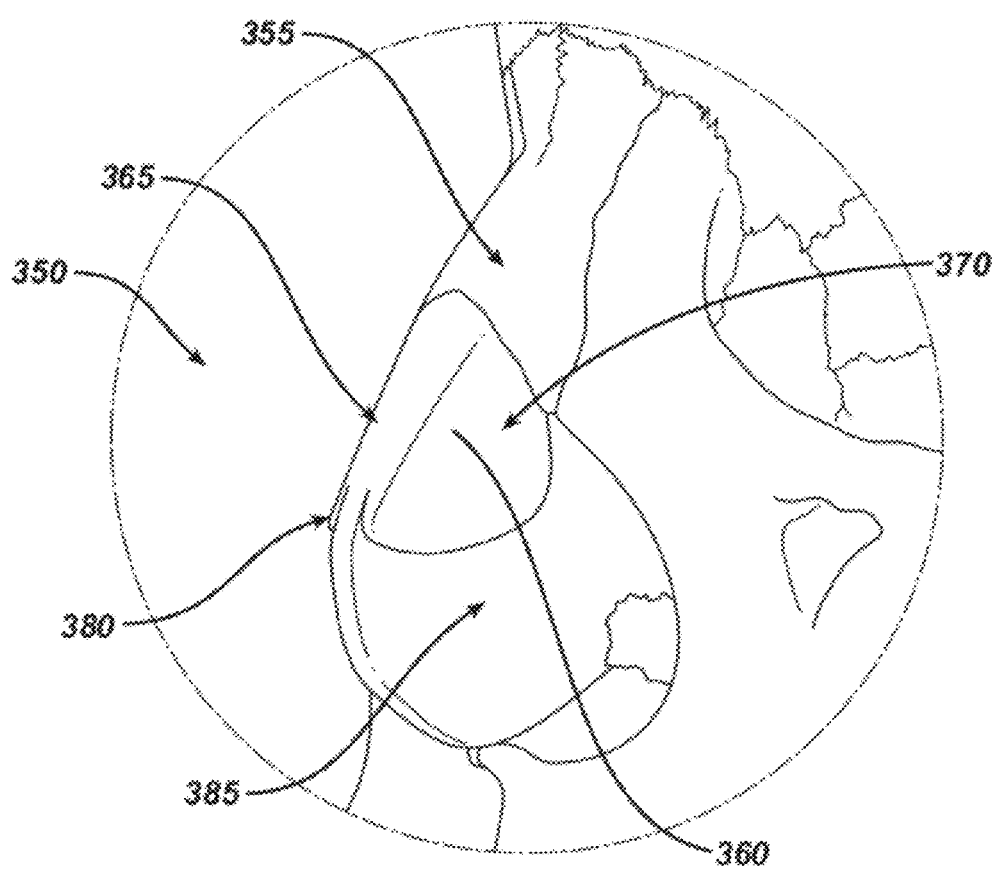
FIGS. 11 and 11A are illustrations of the anatomy of the human nose, specifically showing the structure of the internal nasal valve.
Figure 11A:
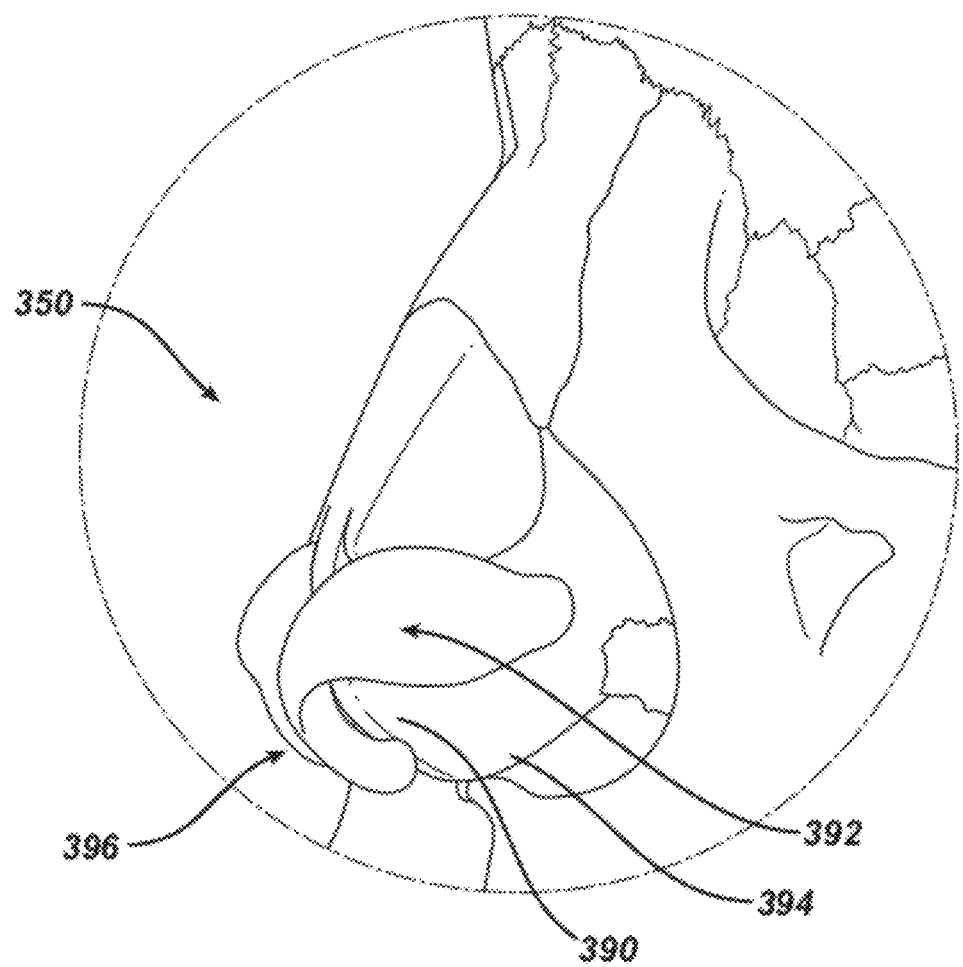

Referring now to FIG. 11 and FIG. 11A, an anatomical illustration of the nasal valve structure of a human nose 350 is illustrated. As previously mentioned, one of the main functions of the nose is breathing. The nose is part of the respiratory system. The airways from each nostril converge in the back of the nose in the upper throat area, from which point the air is drawn towards the nasopharyx, down the trachea, through the bronchi, and into the lungs. The term "nasal valves" is often used in rhinoplasty. These are not actually valves, in the traditional sense. Rather, they are the junction of where two specific internal nasal structures come together. There are two valves that influence the ease in which air is inspired through the nose. The nose 350 is seen to have nasal bones 355. Adjacent to nasal bone 355 is the internal nasal valve 360. Nasal valve 360 is the internal junction 365 of the upper lateral cartilages 370 and the septum 380, this is the narrowest part of the nasal airway 385 and the most important valve area. The second valve is the external nasal valve 390. The valve 390 is composed of the lower alar cartilage 392, nasal floor 394 and the columella 396.

One reason that the internal and external valves of the nose are important in rhinosurgery is that these regions can sometimes collapse. The collapse may be due to weakness of the lateral nasal or side walls, as a complication of previous surgery, or due to trauma. The lateral nasal or side walls are formed by the nasal bones 355 and the upper lateral cartilage 370. The techniques used to correct nasal obstruction due to nasal valve collapse can be broadly divided into two categories: increasing the cross-sectional area in the valve and strengthening the lateral side walls.

Figures 12A, 12B:
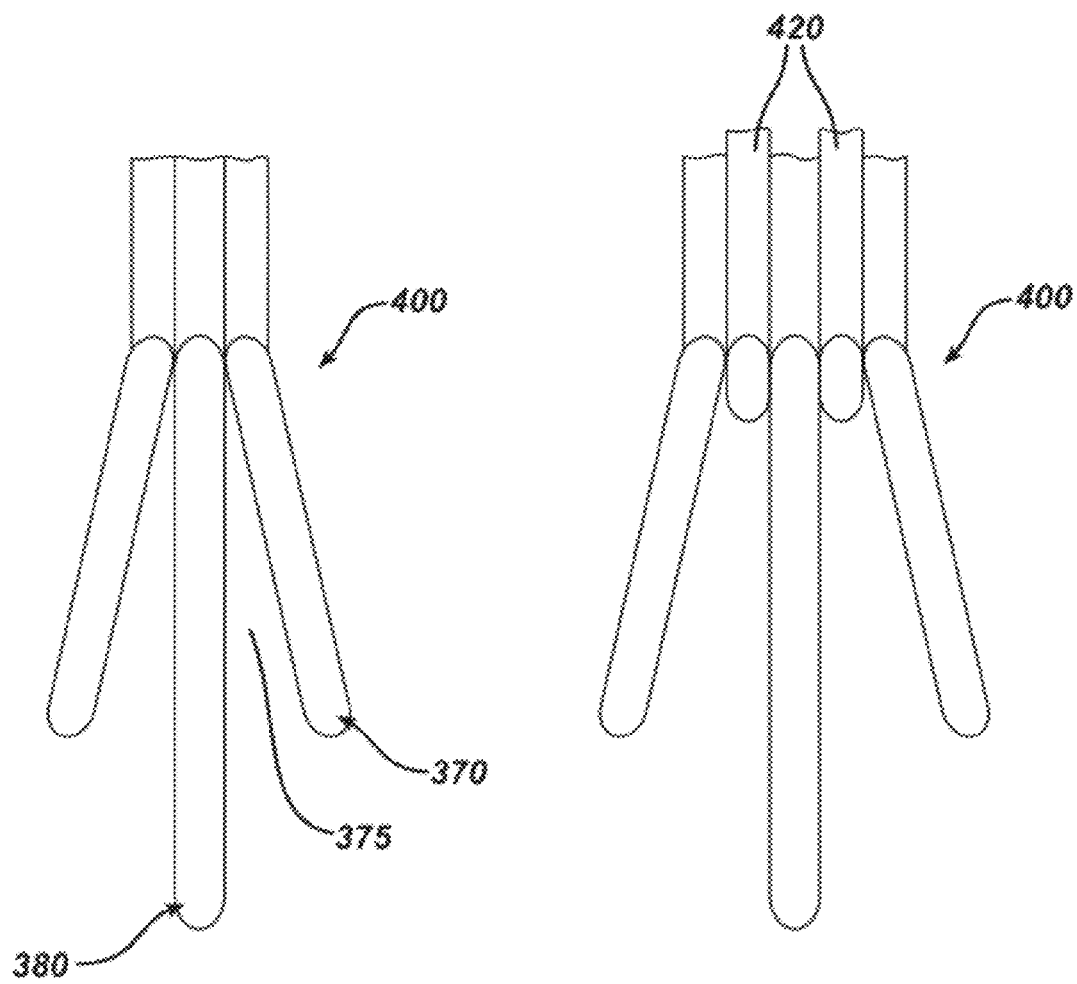
FIGS. 12A and 12B are schematic diagrams illustrating the internal nasal valve with a deficient opening, and the nasal valve after a nasal spreader graft device of the present invention has been implanted, with the obvious improvement in the size of the valve opening seen.

Spreader grafts are used to restore or maintain the internal nasal valve, straighten a deviated dorsal septum, improve the dorsal aesthetic lines, and reconstruct an open roof deformity. A schematic of an internal nasal valve 400 is seen in FIG. 12A. The nasal valve 400 is seen to consist of septum 380 and upper lateral cartilages 370. The nasal valve 400 is seen to have the following defect: the angle 375 between the septum 380 and the upper lateral cartilage 370 is less than the normal range of 10-15 degrees. Using spreader graft implant devices 420 of the present invention, the defect is seen to be corrected after the devices 420 have been implanted on either side of the septum 380. Referring to FIG. 13A, a schematic of a nose 470 having a deviated septum 472 is illustrated. The nose is seen to have the following structures: the internal junction 482 of the upper lateral cartilages 480 and the septum 472, sitting just above or behind the tip 474 of the nose 470. This is the narrowest part of the nasal airway 485, the lower alar cartilage 492, and nasal floor 494. In FIG. 13B, the deviated septum 472 is seen to have been straightened via a surgical procedure wherein graft spreader implants 495 of the present invention are implanted on either side of septum 472 and sutured in place in a conventional manner using sutures 498.

Conventional spreader grafts are typically paired, longitudinal autologous cartilage grafts placed between the dorsal septum and the upper lateral cartilages in a sub-mucoperichondrial pocket. Septal cartilage is the preferred source of the grafts, whose length and shape may vary depending on the indication. The grafts are typically suture-fixated to the septum before re-approximation of the upper lateral cartilages to the septum-spreader graft complex.

Figure 14:
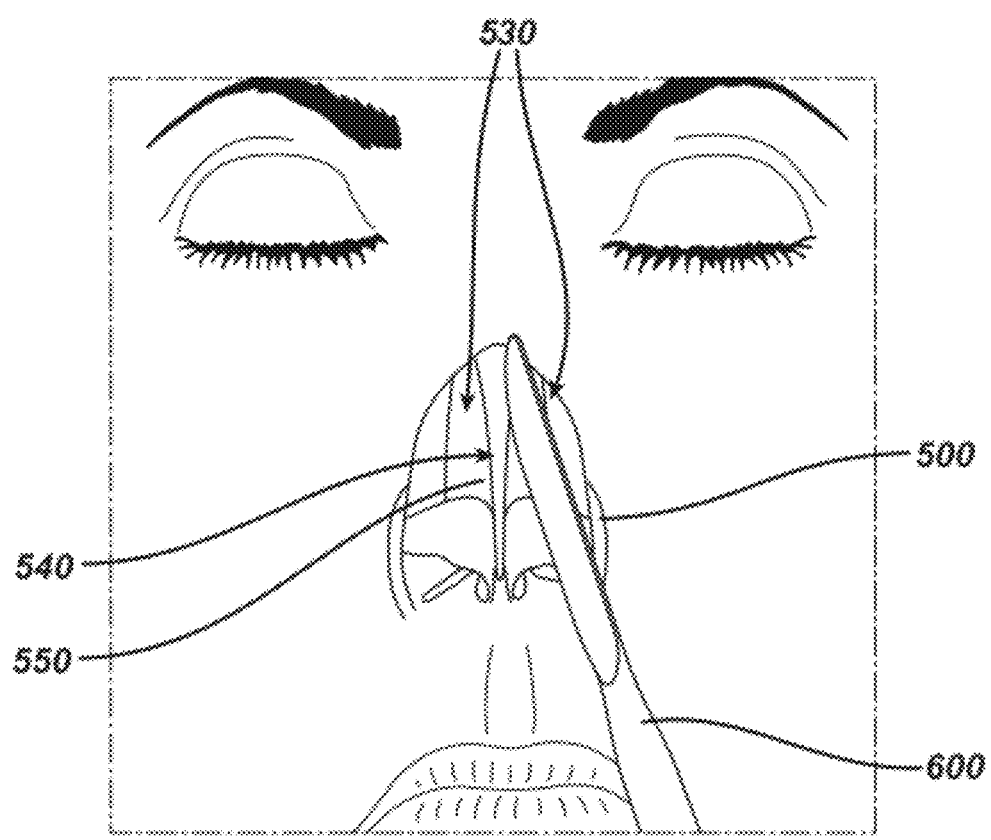
FIG. 14 is an illustration of a surgical procedure to implant a nasal spreader graft implant of the present invention, wherein the nasal valve structure has been uncovered by the surgeon prior to the upper lateral cartilages being separated from the nasal septum.
Figure 15:
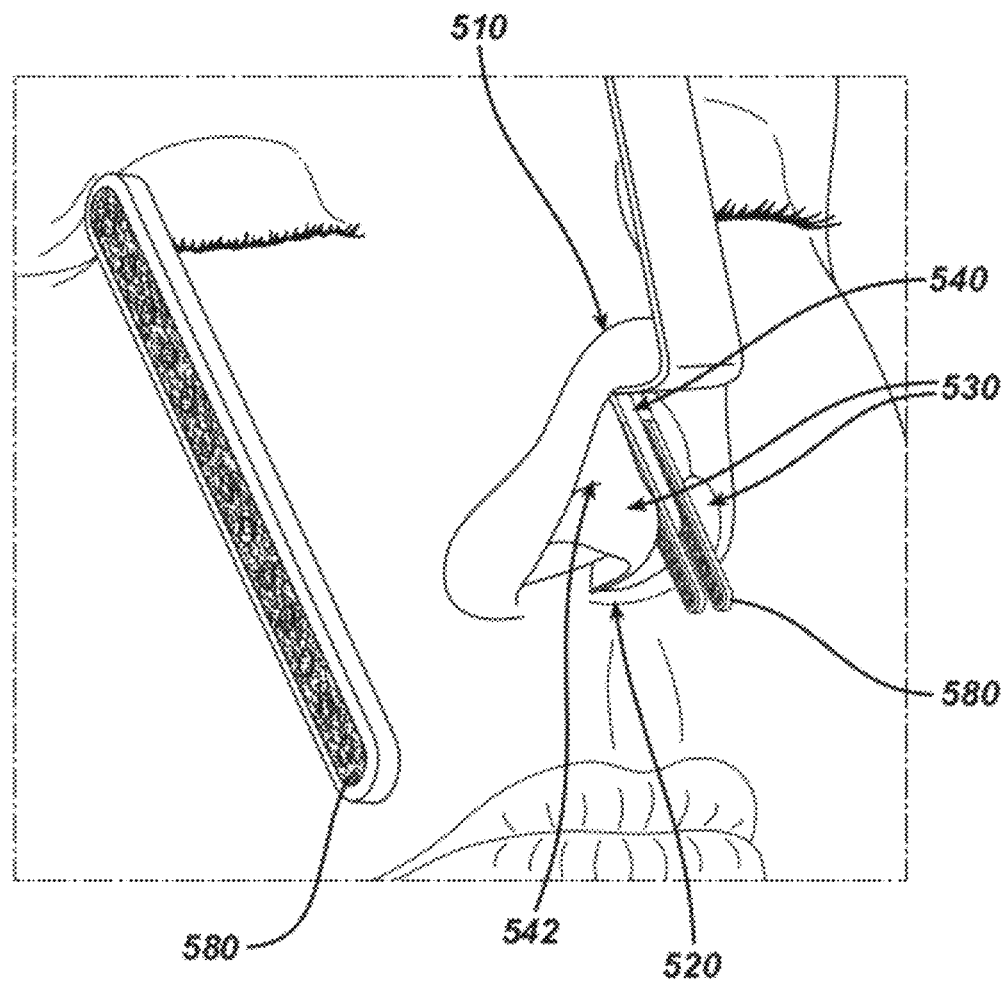
FIG. 15 illustrates the spreader grafts implanted on opposed sides of the septum prior to suturing and trimming
Figure 16:
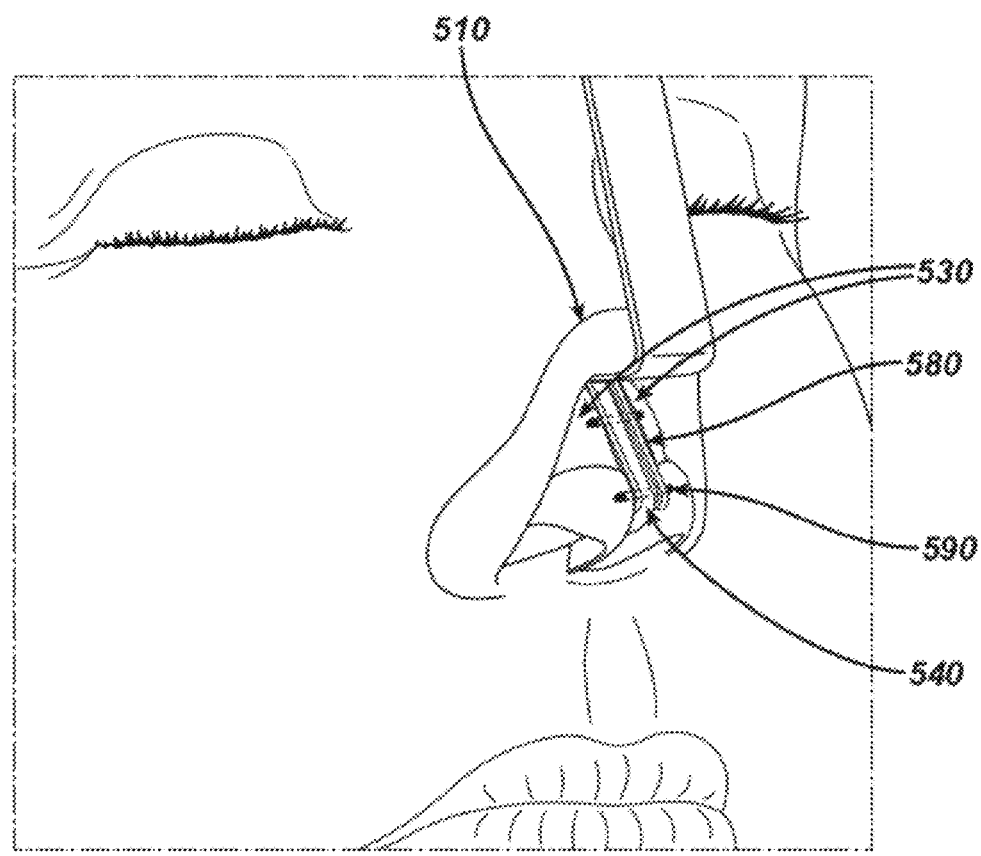
FIG. 16 illustrates the spreader grafts sutured in place and trimmed to complete the corrective nasal valve procedure, immediately prior to returning and affixing the skin envelope and accompanying soft tissue of the patient's nose.

The novel nasal spreader graft implants devices of the present invention can be used in surgical procedures using conventional techniques to correct nasal valve and septum defects as previously discussed. A typical surgical procedure is illustrated in part in FIGS. 14-16. Using an open approach technique for rhinoplasty, a trans-columellar incision is made in the nose 500 of a patient using a conventional cutting device such as a scalpel 600. The skin and soft tissue envelop 510 above the incision is released from the tip 515 of the nose 500 and the columella 520, exposing the lower lateral cartilages 560. Dissection and elevation is continued until the upper lateral cartilages 530 are exposed. The upper lateral cartilages 530 are separated from the septum 540. Mucoperichondrial flaps 545 are elevated from the junction 542 of the upper lateral cartilages 530 and the septum 540 to prevent injury to the mucosal lining 550. Spreader graft implants 580 of the present invention, having the appropriate or desired thickness, are trimmed to the desired size and placed from dorsal approach.

The novel spreader grafts 580 of the present invention are fixated to the septum 540 using sutures 590 or other conventional, appropriate fixation devices such as staples and tacks, or glues or adhesives, and the upper lateral cartilages 530 are re-approximated to the septum-spreader graft complex. The procedure may involve placing of additional cartilage grafts and the use of various sutures for modifying nasal structures depending on the desired functional and aesthetic outcome. The procedure is complete by redraping the soft tissue envelope 510 and closing the columellar incision. Other variations of the procedure may include using graft spreader devices of the present invention having spreader plate members, and utilizing the appropriate thickness and number of spreader plates to achieve the desired spreader graft implant size.

The following examples are illustrative of the principles and practice of the present invention although not limited thereto.

Example 1

Figure 5:
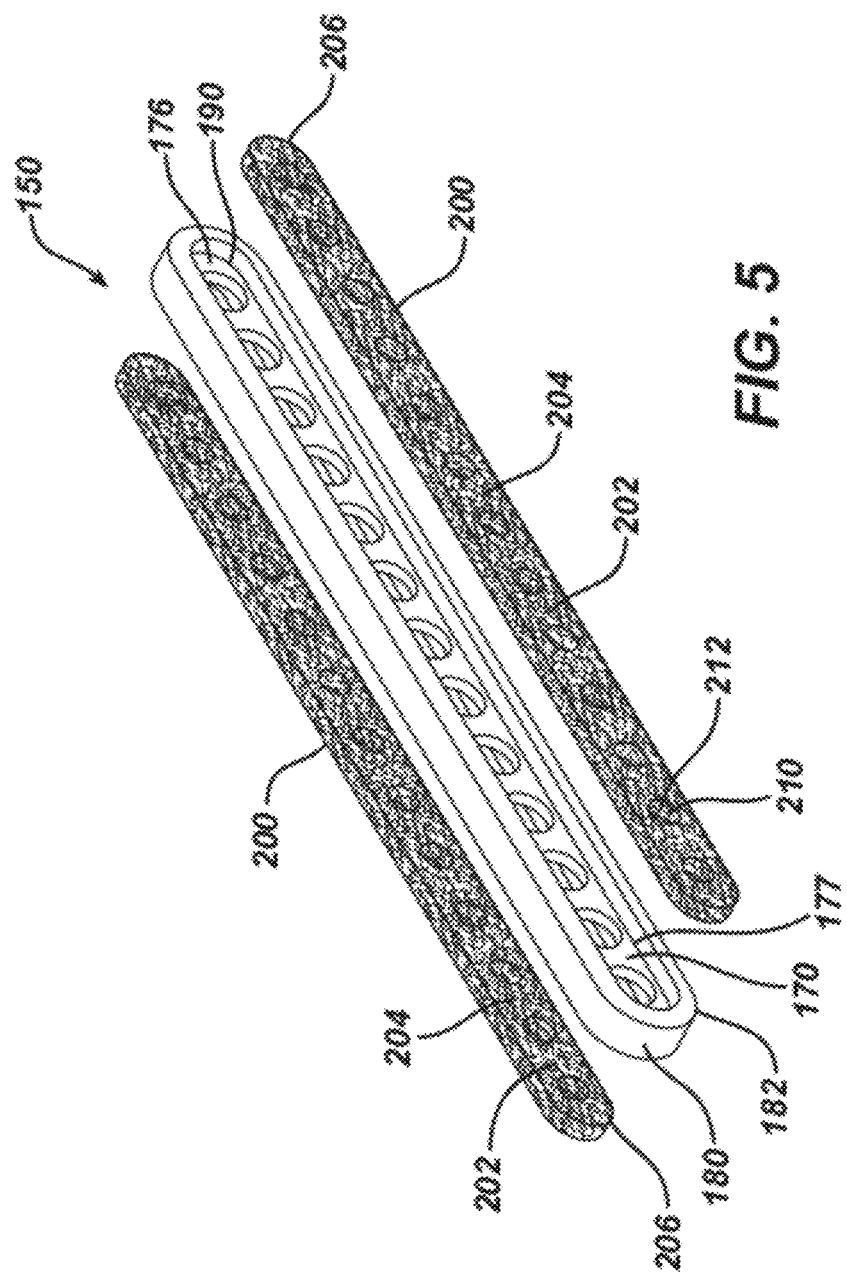
FIG. 5 is an exploded perspective view of an alternate embodiment of a spreader graft implant device of the present invention having a core plate member with a continuous outer peripheral flange and tissue ingrowth plate inserts.
Figure 6A:
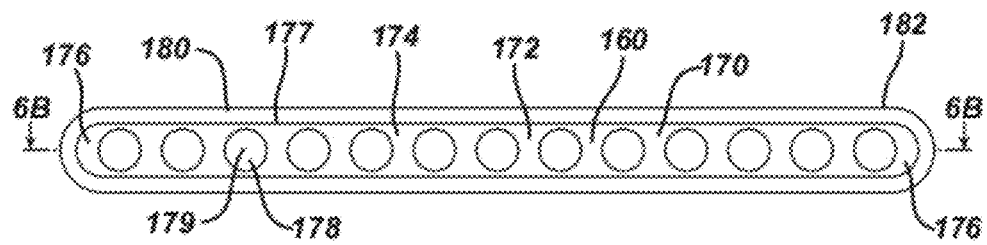
FIGS. 6A-C illustrate side, top longitudinal cross-section, and perspective views, respectively, of the core plate member of FIG. 5.
Figure 6B:
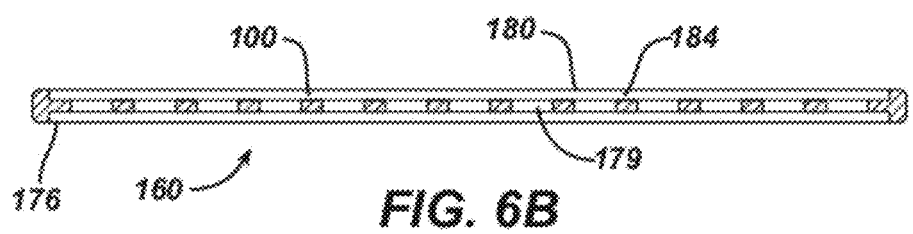
Figure 6C:
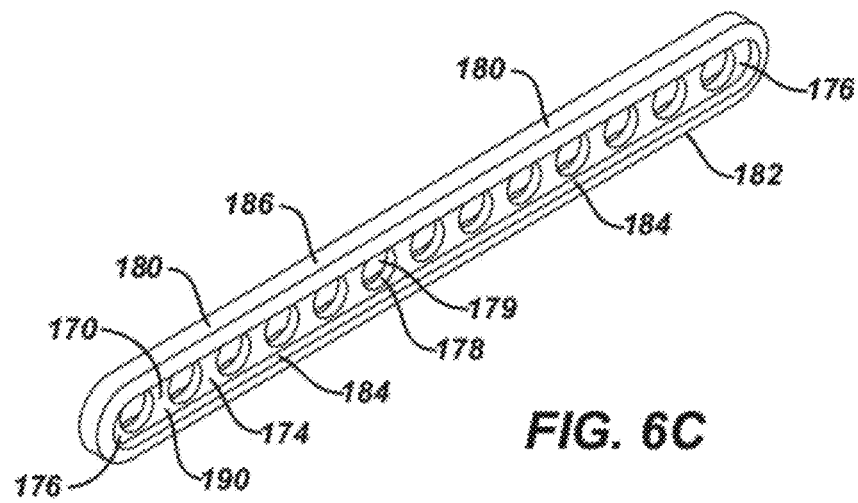
Figure 7A:
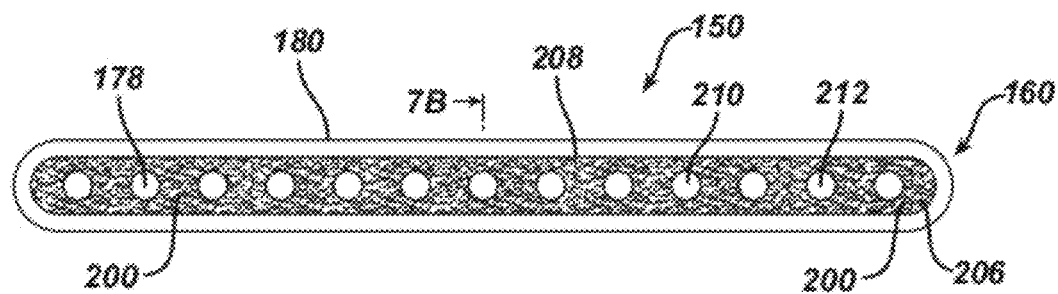
FIGS. 7A-C illustrate side, cross-sectional, and perspective views, respectively, of the assembled spreader graft implant device of FIG. 5.
Figure 7B:
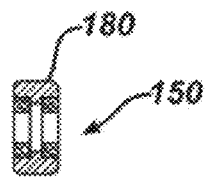
Figure 7C:
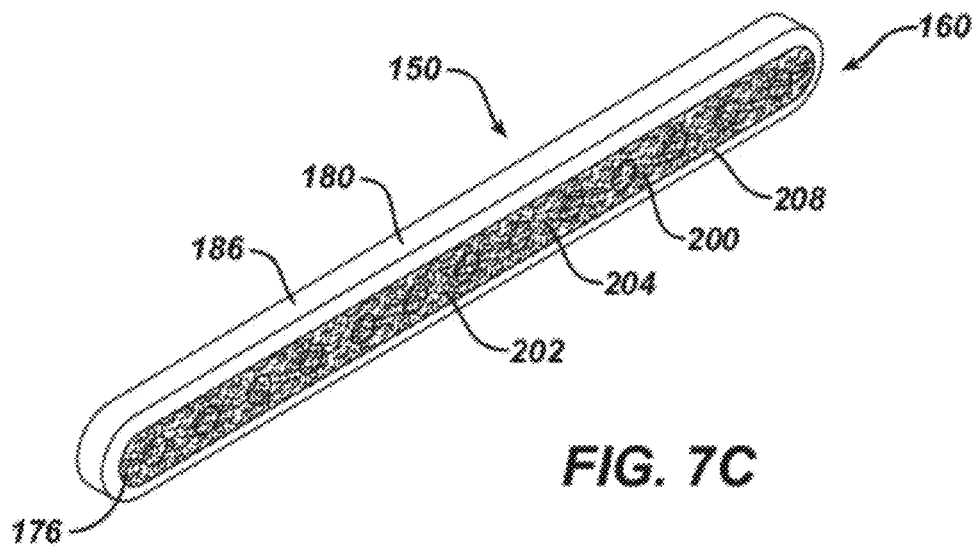
Figure 9A:
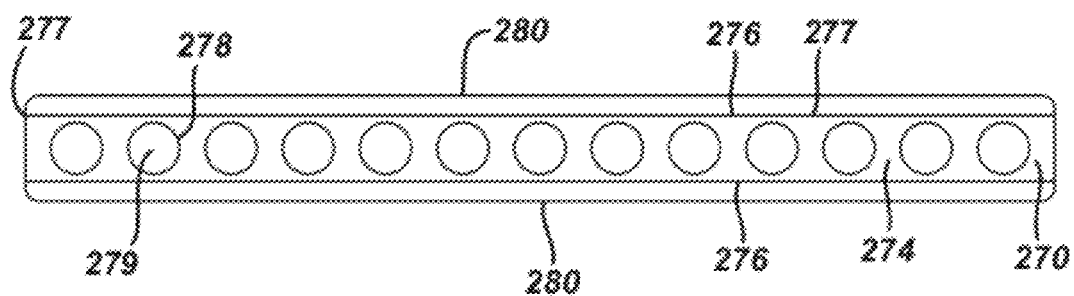
FIGS. 9A-C illustrate side, end and perspective views, respectively, of the I-beam core plate member of FIG. 8.
Figure 9B:
Figure 9C:
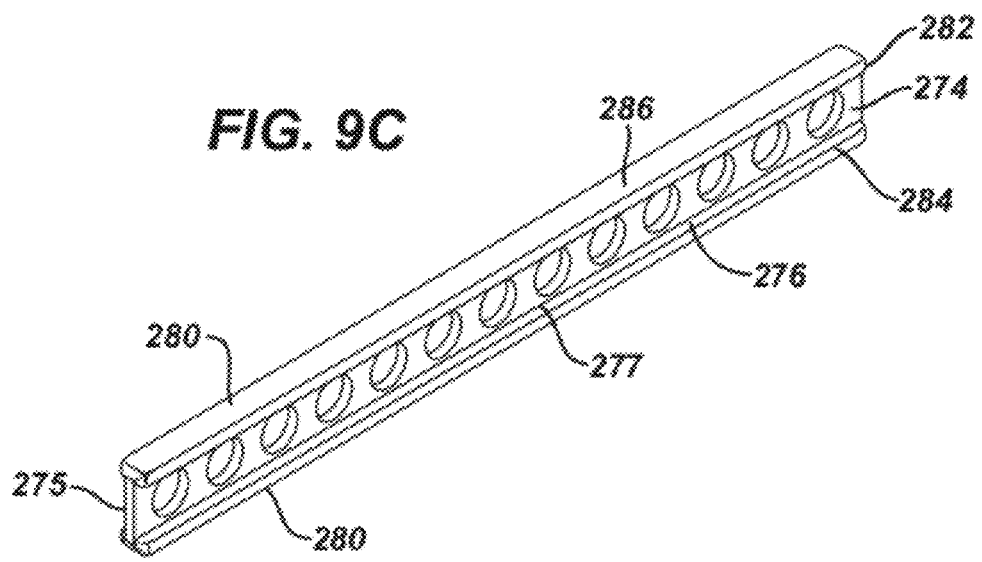
Figure 10A:
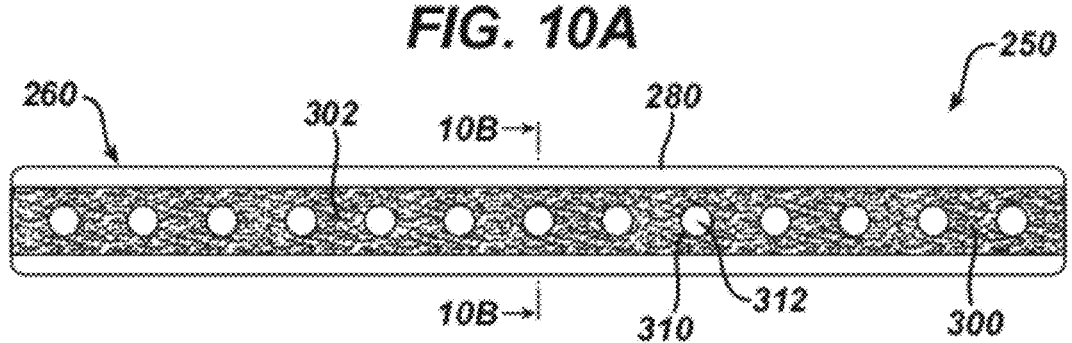
FIGS. 10 A-C illustrate side, cross-sectional, and perspective views, respectively, of the assembled spreader graft implant device of FIG. 8.
Figure 10B:
Figure 10C:
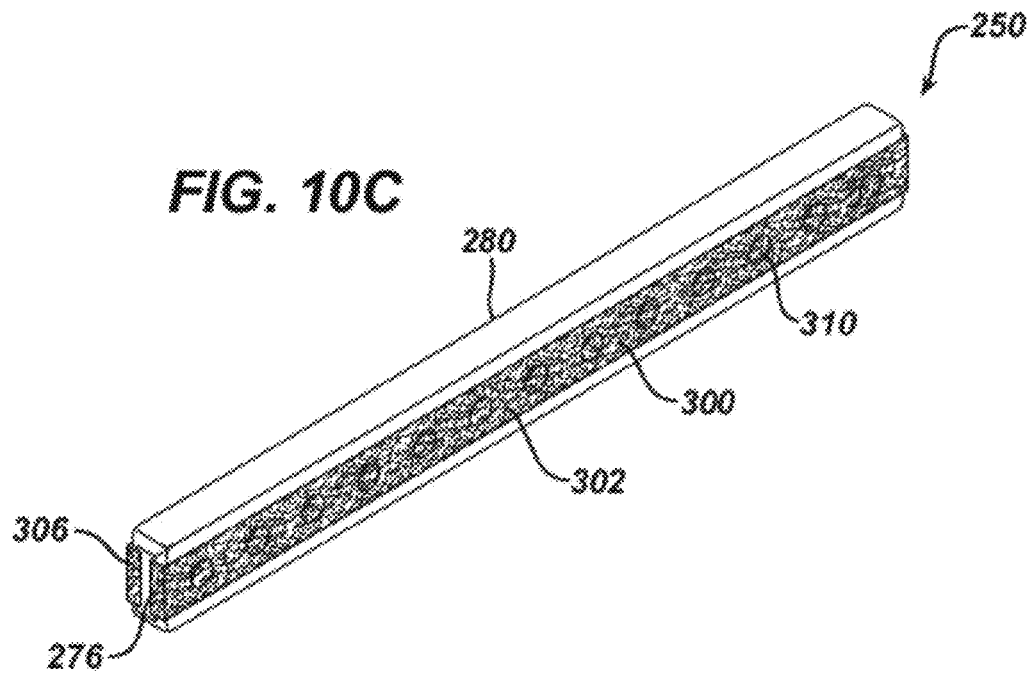

In this example, a multi-layer spreader graft of 1.5 mm width was constructed from an I-beam core plate member and two non-woven spreader plates. The configuration of the graft is seen in FIG. 5. The I-beam core plate member was injection molded from natural poly(p-dioxanone) having about 70,000 Daltons weight-average molecular weight. A NISSEI Injection Machine Model NEX30 was used, which was made by NISSEI Plastic Industrial Company, Ltd. The injection machine nozzle zone temperature was set at 132° C. The mold temperature was in the range of 44 to 46° C.

The molded I-beam had a length of about 40 mm, a height of about 4.0 mm, a thickness of about 0.5 mm at the center portion of the core plate and a flange having an overall width of 1.5 mm and thickness of 0.75 mm at the top and bottom, respectively, of the core plate.

The outer spreader or tissue ingrowth plates were made of polydioxanone nonwoven fabrics of about 0.6 mm thickness. The PDS nonwoven fabrics were manufactured as follows. On a 15-inch melt blown nonwoven line of the type described hereinbelow, equipped with single screw extruder, a polymer of poly(p-dioxanone) with 70,000 Daltons weight-average molecular weight was extruded into meltblown nonwovens. This process involved feeding the solid polymer pellets into a feeding hopper on an extruder. The extruder had a 1" single screw with three heating zones which gradually melted the polymer and extruded the molten polymer through a connector or transfer line. Finally, the molten polymer was pushed into a die assembly containing many capillary holes out of which emerge small diameter fibers. The fiber diameter was attenuated at the die exit as the fiber emerged using high velocity hot air. About 6 inches from the die exit was located a rotating collection drum on which the fibrous web was deposited and conveyed to a wind-up spool. The melt blown line was of standard design as described by Buntin, Keller and Harding in U.S. Pat. No. 3,978,185, the contents of which are hereby incorporated by reference in their entirety. The die used had 374 capillary holes with a diameter of 0.020 inch per hole.

The nonwoven fabrics were cut into small pieces of precise dimensions using an ultrasonic cutting machine Chase FS-90 manufactured by Chase Machine and Engineering, Inc. The cut nonwoven spreader plates had a width of 2.46 mm and a length of 3.95 mm, which fitted well into the recessed areas at the left and right sides of the I beam core plate member.

Figure 17A:
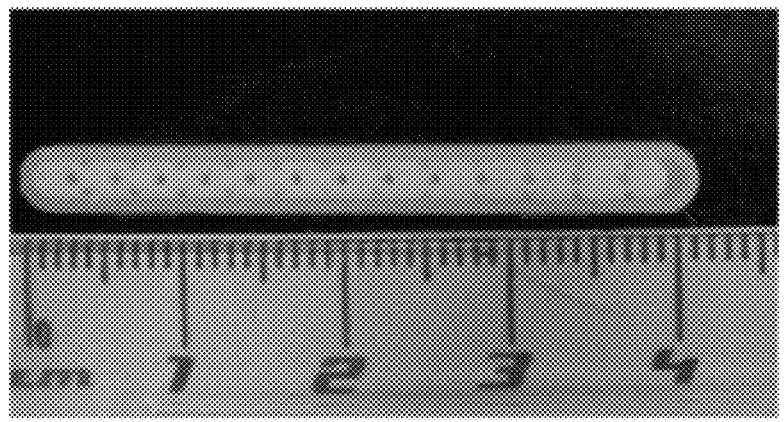
FIG. 17A is photograph of a spreader graft device of the present invention, manufactured in accordance with Example 1.

The cut nonwoven tissue ingrowth plates were then welded at perimeters to the I-beam core plate using an ultrasonic machine Model X2000, manufactured by Branson Ultrasonics Corp. FIG. 17A shows a picture of the assembled spreader graft that was made from poly(p-dioxanone) core plate member and poly(p-dioxanone) nonwoven tissue ingrowth plates in accordance with the present example. The overall thickness of the assembled device was about 1.5 mm. Upon implantation of this device in a patient's nose between the septum and the upper lateral cartilage, new soft tissue will ingrow into the nonwoven structure gradually, and mature when the poly(p-dioxanone) fibers are substantially absorbed in about 3 to 5 months. The poly(p-dioxanone) core plate member provides sufficient mechanical support for over about 8 to 10 weeks following implantation in a patient. The poly(p-dioxanone) core plate will be essentially absorbed in about 5 to 6 months following implantation.

Example 2

Figure 17B:
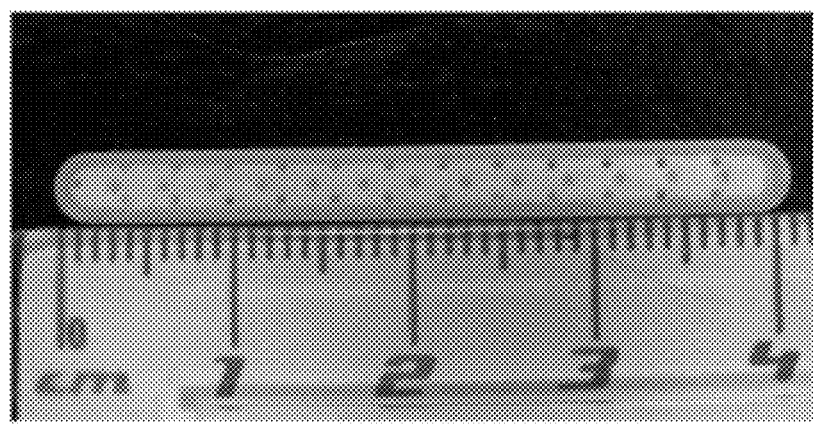
FIG. 17B is photograph of a spreader graft device of the present invention, manufactured in accordance with Example 2.

A device of the present invention was made from the same polymer, poly(p-dioxanone), and by the same manufacturing methods as described for Example 1. The only differences were that: a) the overall width of the I beam core plate member was 2.0 mm instead of 1.5 mm, and b) the thickness of the poly(p-dioxanone) nonwoven tissue ingrowth plate was about 0.9 mm. The device made in accordance with this example is seen in FIG. 17B. The overall configuration was the same as that of Example 1.

Example 3

A spreader graft device of the present invention was made using the same manufacturing methods as described for Example 1, except that the polymer of the I-beam core plate member (having a width of 1.5 mm) was a blend of 20% by weight poly(p-dioxanone) and 80% by weight of 85/15 PLGA (designated as PALG20-85). The injection machine nozzle zone temperature was in the range of 171-173° C. and the mold temperature was in the range of 28-32° C.

Figure 18A:
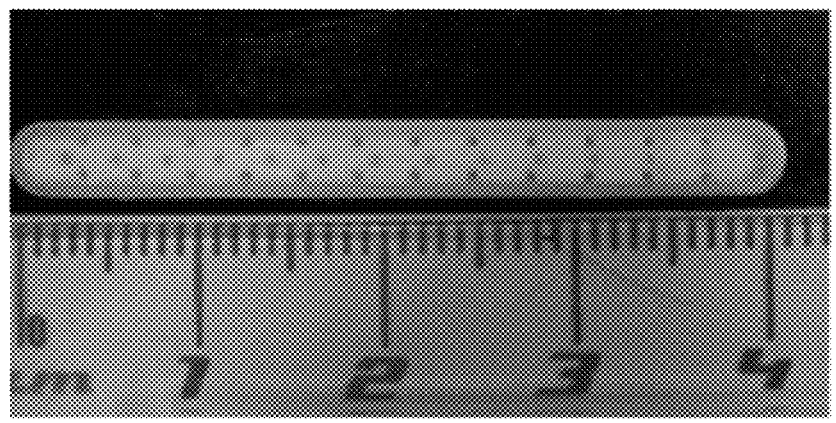
FIG. 18A is photograph of a spreader graft device of the present invention, manufactured in accordance with Example 3.

Because PALG20-85 polymer has a slow degradation rate in vitro or in vivo, the core plate made from PALG20-85 had significantly greater breaking strength retention (BSR) in vivo than that of poly(p-dioxanone) core plate. At 10 weeks in vitro, the PALG20-85 plate had about 60% of BSR while the poly(p-dioxanone) core plate had less than about 20% BSR. PALG20-85 is predicted to be essentially absorbed in about 11 months. For patients who need mechanical support for more than 10 weeks post surgery, the PALG20-85 core plate would be indicated rather than the poly(p-dioxanone) core plate. Because the nonwoven plate is provided as scaffold for early tissue ingrowth, it is preferred to have poly(p-dioxanone) nonwoven spreader or ingrowth insert plates even when PALG20-85 is used for the core plate member. A photograph of the device made in accordance with this example is seen in FIG. 18A.

Example 4

Figure 18B:
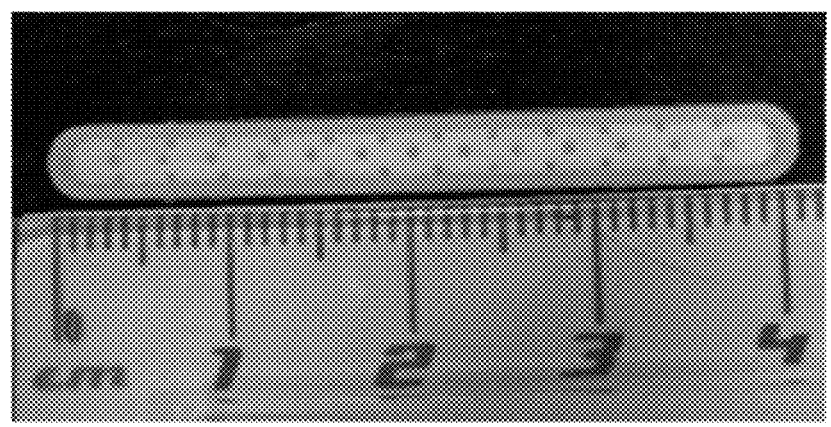
FIG. 18B is photograph of a spreader graft device of the present invention, manufactured in accordance with Example 4.

A spreader graft device was made in a similar manner to that of Example 3, except that the width of the device was 2.0 mm. A photograph of the device made in accordance with this example is seen in FIG. 18B.

Example 5

A patient is prepared for nasal reconstructive surgery in a conventional manner including the steps of injecting a local anesthetic, making marginal and/or columellar incisions, elevation of the soft tissue skin envelop and developing appropriate dissection planes. The procedure is continued by placing appropriate grafts and using suture techniques to achieve the desired functional and aesthetic results depending on the preoperative assessment and surgical plan. The patient has a middle vault deficiency which can result in significant functional and cosmetic implications. The condition requires surgical intervention and repair. A spreader graft device of the present invention having a configuration as seen in FIG. 17B is implanted by a surgeon in the following manner: gaining access to the nasal dorsum; separating the upper lateral cartilages from the nasal septum; developing muchoperichondrial flaps at the junction of the septum and the ULC; placing the spreader graft device and, fixating the spreader graft device to the septum and the ULC. If no other grafts or structure modifications are required the procedure is completed by redraping the soft tissue over the nasal structure and closing the marginal and columellar incision. Alternatively, the spreader graft device may be placed by an endonasal approach by developing a tight subperichondrial pocket between the upper lateral cartilages and the septum and tunneling the spreader graft device in the pocket.

The novel nasal graft spreader devices of the present invention have many advantages when used in rhinoplasty surgical procedures. The advantages include: shorter operating time with an off-the-shelf product; better predictability of the outcome with desirable and consistent width of the spreader graft; elimination of the need for autografts and allografts; and, lower risk of long term complications due to complete absorption after the mechanical support is no longer required of the implanted graft.

Although this invention has been shown and described with respect to detailed embodiments thereof, it will be understood by those skilled in the art that various changes in form and detail thereof may be made without departing from the spirit and scope of the claimed invention.

We claim:

1. A bioabsorbable, nasal valve spreader implant device, comprising:
    an elongated core plate member having first and second opposed lateral sides, the plate member having first and second opposed outer surfaces, the plate member having opposed ends, the plate member having a periphery and a plurality of openings including at least one engagement opening extending through the first and second outer surfaces of the plate member; and,
    at least two elongated spreader plate members, each having first and second opposed lateral sides, the at least two elongated spreader plate members having outer surfaces, and at least one snapping pin member extending from at least one outer surface of each of said elongated spreader plate members, and a plurality of openings extending through said spreader plate members,
    wherein the elongated spreader plate members are each secured to said core plate member by engaging the at least one snapping pin member of each elongated spreader plate member with said at least one engagement opening in the core plate member, such that one elongated spreader plate member is disposed on said first outer surface of said elongated core plate member and a second elongated spreader plate member is disposed on said second outer surface of said elongated core plate member;
    wherein the core plate member and spreader plate members comprise a bioabsorbable polymer.

2. The device of claim 1, wherein the bioabsorbable polymer is selected from the group consisting of poly(p-dioxanone), co-polymers of poly(lactide-co-glycolide), and blends thereof.

3. The device of claim 2, wherein the bioabsorbable polymer comprises a blend of poly(p-dioxanone) and poly(lactide-co-glycolide) copolymer.

4. The device of claim 1, wherein the core plate member additionally comprises a snapping pin member extending from one of the first or second opposed outer surfaces, the pin member engageable by an engagement opening on the spreader plate member.

5. The device of claim 1, wherein the bioabsorbable polymer has a BSR of about at least 40% at 4 weeks after implantation.

6. The device of claim 1, additionally comprising a flange member extending about at least part of the periphery of the core plate member and forming a cavity above the outer surface of each lateral side, wherein at least part of the spreader plate member is contained in the cavity.

7. The device of claim 1, wherein the bioabsorbable polymer has an in vivo absorption time of about 30 days to about 1 year.

8. The device of claim 1, additionally comprising a coating on at least part of the surfaces.

9. The device of claim 1, wherein the bioabsorbable polymer comprises a foam.

10. The device of claim 1, additionally comprising micropores.

11. The device of claim 1, additionally comprising a therapeutic agent.

12. The device of claim 1, additionally comprising microfibers on the surfaces.

13. The device of claim 1, wherein the core plate member has a rectangular cross-section.

14. The device of claim 6, wherein the core plate member has an I-beam cross-section.

15. The device of claim 1, wherein each of the plate members have a thickness of about 0.1 mm to about 0.5 mm.

16. The device of claim 1, wherein the core plate member and the spreader plate members each have a length, and the length of the core plate member is about the same or slightly greater than the length of the spreader plate members.

17. The device of claim 1, wherein the bioabsorbable polymer comprises a blend of about 20 wt % to about 60 wt % poly(p-dioxanone) and about 80 wt % to about 40 wt % 85/15 poly(lactide-co-glycolide) copolymer.

18. A method of performing a surgical procedure comprising the steps of;
surgically exposing the lower lateral cartilage of a nose of a patient, the nose having a caudal border bone and lower lateral cartilages; and,
implanting a nasal spreader graft device between the caudal border bone and the lower lateral cartilages of the nose, wherein the device comprises:
an elongated core plate member having first and second opposed lateral sides, the plate member having first and second opposed outer surfaces, the core plate member having opposed ends, the plate member having a periphery and a plurality of openings including at least one engagement opening extending through the first and second outer surfaces of the core plate member; and,
at least two elongated spreader plate members, each having first and second opposed lateral sides, the at least two elongated spreader plate members having outer surfaces, and at least one snapping pin member extending from at least one outer surface of each of said elongated spreader plate members, and a plurality of openings extending through said spreader plate member,
wherein the elongated spreader plate members are each secured to said core plate member by engaging the at least one snapping pin of each elongated spreader plate member with said at least one engagement opening in the core plate member, such that one elongated spreader plate member is disposed on said first outer surface of said elongated core plate member and a second elongated spreader plate member is disposed on said second outer surface of said elongated core plate member;
wherein the core plate member and elongated spreader plate members comprise a bioabsorbable polymer.

19. The method of claim 18, wherein the bioabsorbable polymer is selected from the group consisting of poly(p-dioxanone), copolymers of poly(lactide-co-glycolide), and blends thereof.

20. The method of claim 18, wherein the bioabsorbable polymer comprises a blend of poly(p-dioxanone) and poly(lactide-co-glycolide) copolymer.

21. The method of claim 18, wherein the core plate member additionally comprises a snapping pin member extending from one of the first or second opposed outer surfaces, the pin member engage able by an engagement opening on the spreader plate member.

22. The method of claim 18, wherein the polymer has a BSR of about at least 40% at 4 weeks after implantation.

23. The method of claim 18, wherein the device additionally comprises a flange member extending about at least part of the periphery of the core plate member forming a cavity above the top surface of each lateral side, wherein at least part of the spreader plate member is contained in the cavity.

24. The method of claim 18 wherein the polymer has an in vivo absorption time of about 30 days to about 1 year.

25. The method of claim 18, additionally comprising a coating on at least part of the surfaces.

26. The method of claim 18, wherein the plate comprises a foam.

27. The method of claim 18, wherein the device additionally comprises micropores.

28. The method of claim 18 wherein the device additionally comprises a therapeutic agent.

29. The device of claim 1, wherein the device additionally comprises microfibers on the surfaces.

30. The method of claim 18, wherein the core plate member has a rectangular cross-section.

31. The method of claim 23, wherein the core plate member has an I-beam cross section.

32. The method of claim 18, wherein the plate members have a thickness of about 0.1 mm to about 0.5 mm.

33. The method of claim 18, wherein the core plate member and the spreader plate member each have a length, and the length of the core plate member is about the same or slightly greater than the length of the spreader plate member.

34. The method of claim 18, wherein the rhinoplasty comprises a defect correction procedure, and the procedure is selected from the group consisting of correction of deviated septums, correction of constricted nasal valves, removal of humps, repairs of trauma, and corrections of obstructed airways due to scaring or stenos is.

* * * * *